Figure 1:
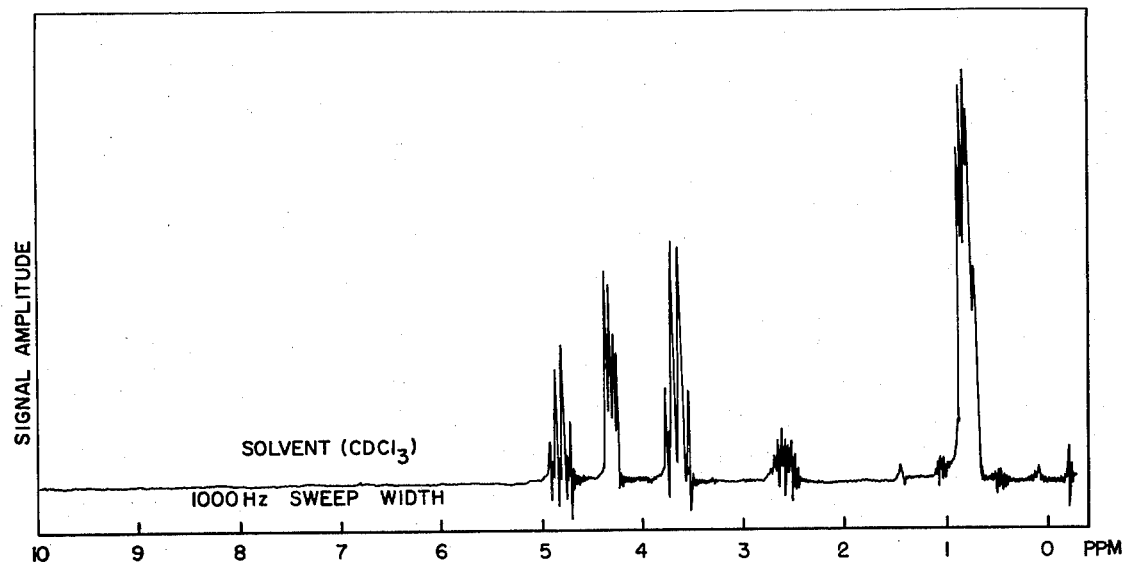

United States Patent [19]

Hall et al.

[11] 3,998,873

[45] * Dec. 21, 1976

[54] PROCESS FOR PREPARING ONE OR MORE ALKYL-2-METHYL PENTENOATES BY MEANS OF HYDROGENATION OF ONE OR MORE ALKYL-2-METHYL-3,4-PENTADIENOATES

[75] Inventors: John B. Hall, Rumson; Denis E. Hruza, Brick Town, both of N.J.

[73] Assignee: International Flavors & Fragrances Inc., New York, N.Y.

[ * ] Notice: The portion of the term of this patent subsequent to July 22, 1991, has been disclaimed.

[22] Filed: Apr. 21, 1975

[21] Appl. No.: 569,853

[52] U.S. Cl. .................... 260/486 R; 260/526 N
[51] Int. Cl.² .................................. C07C 69/54
[58] Field of Search ............ 260/486, 486 R, 526 N

[56] References Cited
OTHER PUBLICATIONS

Roberts and Caseno "Organic Chem." p. 276 1965.
Cram & Hammond "Organic Chem." p. 38 2nd Ed. 1964.

*Primary Examiner*—Paul J. Killos
*Attorney, Agent, or Firm*—Arthur L. Liberman; Harold Haidt

[57] ABSTRACT

A process for producing one or more alkyl-2-methyl pentenoates having the generic structure:

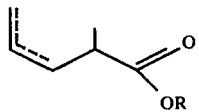

comprising the steps of:

i. Contacting with hydrogen gas one or more alkyl-2-methyl-3,4-pentadienoates having the structure:

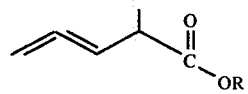

in the presence of a hydrogenation catalyst which may be either of:
 a. Raney Nickel;
 b. Palladium on carbon; or
 c. Palladium on calcium carbonate at a temperature from about 10° C up to about 100° C, a hydrogen pressure from about 5 psig up to about 80 psig, the concentration of said catalyst based on the weight of the starting material, the alkyl-2-methyl-3,4-pentadienoate, being from about 0.1% up to about 10%;

ii. Recovering at least 60% by weight of one or more alkyl-2-methyl-cis-3-pentenoates having the structure:

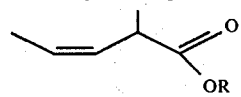

wherein R is alkyl having up to 6 carbon atoms; optionally iii. Separating the ingredients of the resulting chemical composition to obtain ethyl-2-methyl-cis-3-pentenoate; and/or, optionally, iv. Forming one or more carboxylic acids by means of admixing the resulting chemical composition with a basic hydrolysis agent which may be either an aqueous solution of alkali metal hydroxide, or an alcohol solution of an alkali metal hydroxide; and, optionally, v. Re-esterifying the resulting carboxylic acid(s) by reacting said carboxylic acid(s) with an esterifying agent such as an alkanol in the presence of a protonic acid catalyst.

The products produced are useful in altering the organoleptic characteristics (aroma and/or taste) of foodstuffs, foodstuff flavors, chewing gum, medicinal products, tobaccos, flavoring compositions for tobaccos, perfumes, perfume compositions and perfumed articles such as soaps, colognes, cosmetic powders and detergent powders and liquids.

2 Claims, 12 Drawing Figures

EXAMPLE I, FRACTION 10: Ethyl-2-methyl-3,4-pentadienoate

EXAMPLE I, FRACTION 10: Ethyl-2-methyl-3,4-pentadienoate

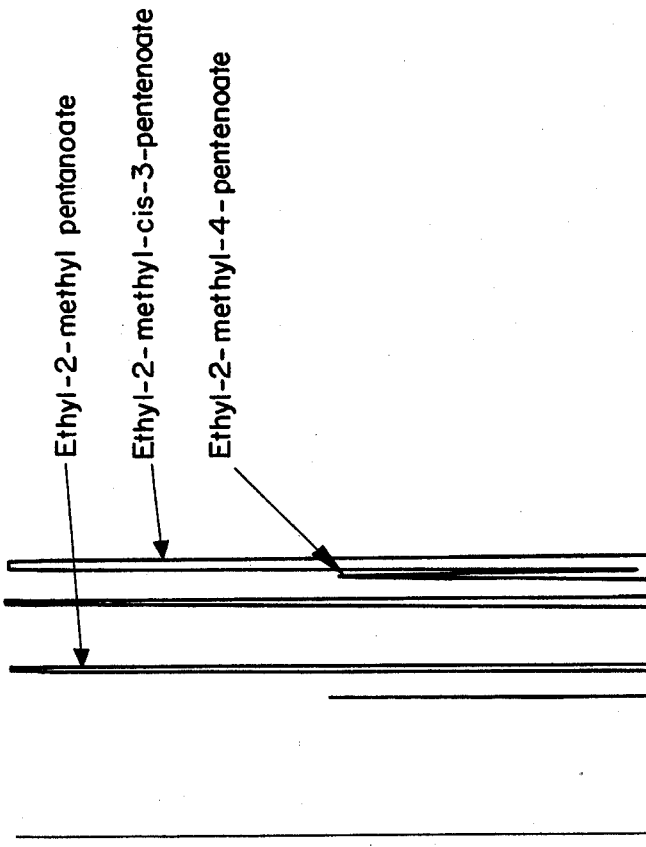

FIG. 3
EXAMPLE II

GLC Curve for mixture of
Ethyl-2-methyl-4-pentenoate;
Ethyl-2-methyl-cis-3-pentenoate;
and
Ethyl-2-methyl pentanoate
produced by hydrogenation of
Ethyl-2-methyl-3,4-pentadienoate
with Pd/C catalyst

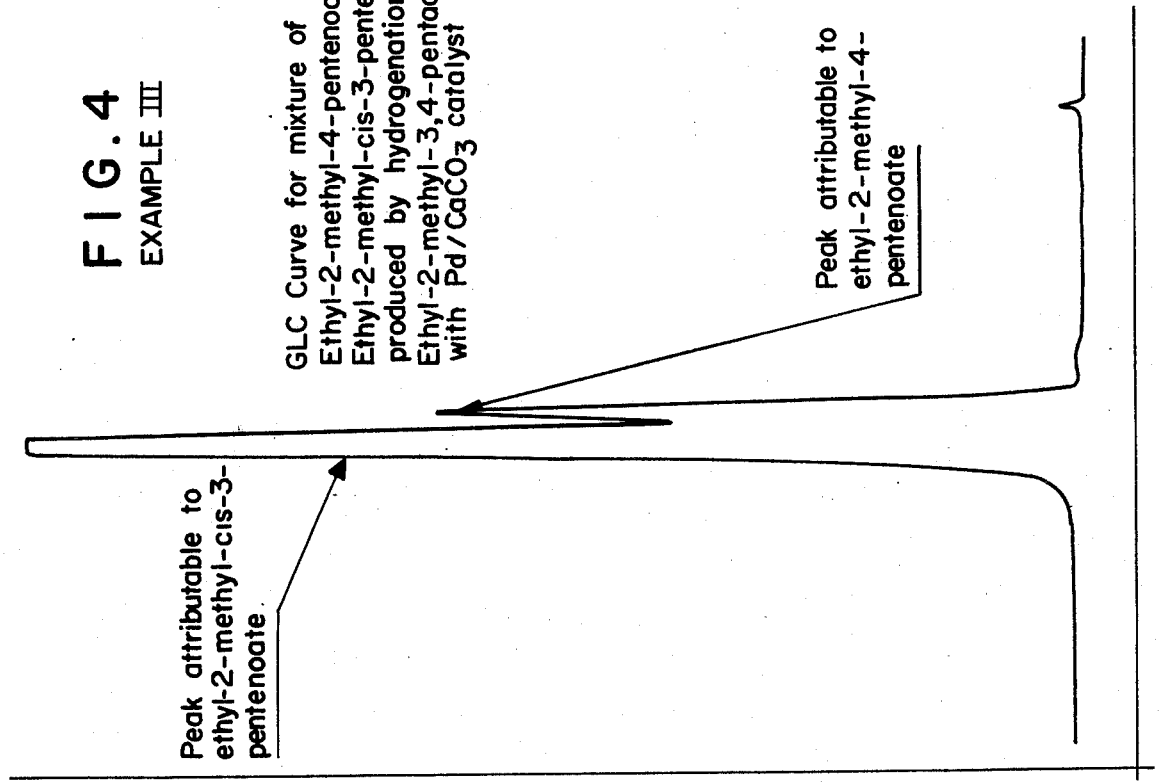

FIG. 4
EXAMPLE III

GLC Curve for mixture of
Ethyl-2-methyl-4-pentenoate and
Ethyl-2-methyl-cis-3-pentenoate
produced by hydrogenation of
Ethyl-2-methyl-3,4-pentadienoate
with Pd/CaCO₃ catalyst

EXAMPLE IV

EXAMPLE VI  Hexyl-2-methyl-3,4-pentadienoate

EXAMPLE VI , Hexyl-2-methyl-3,4-pentadienoate

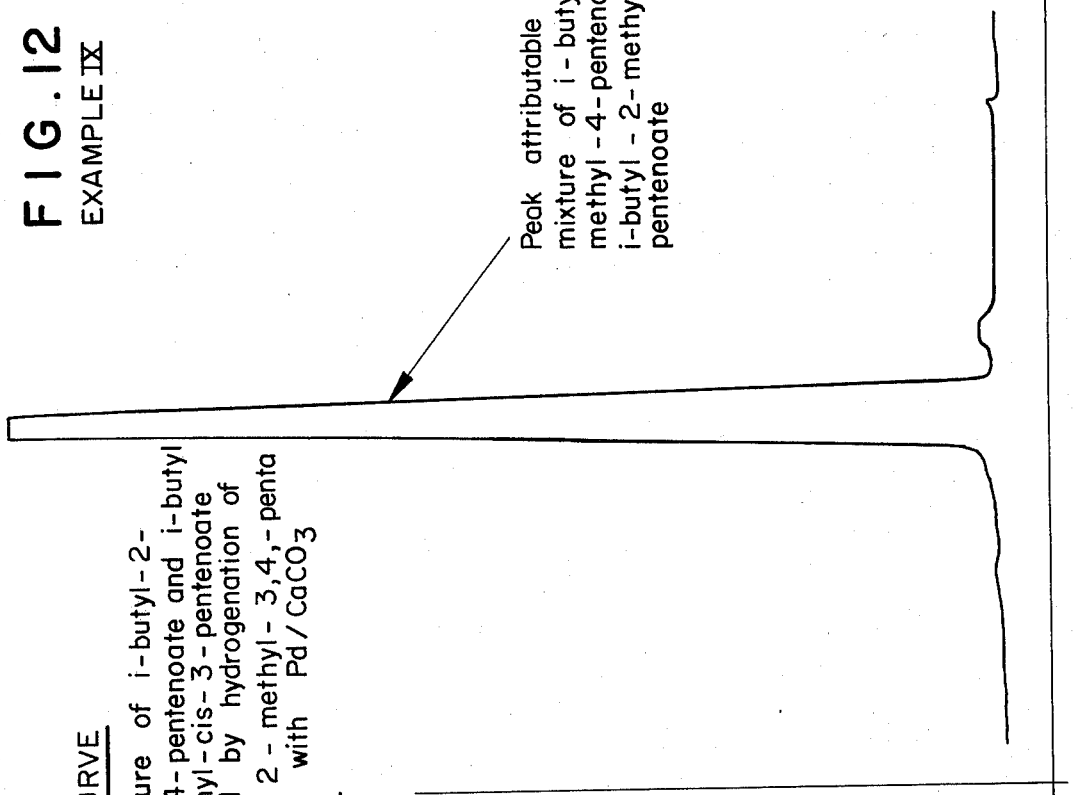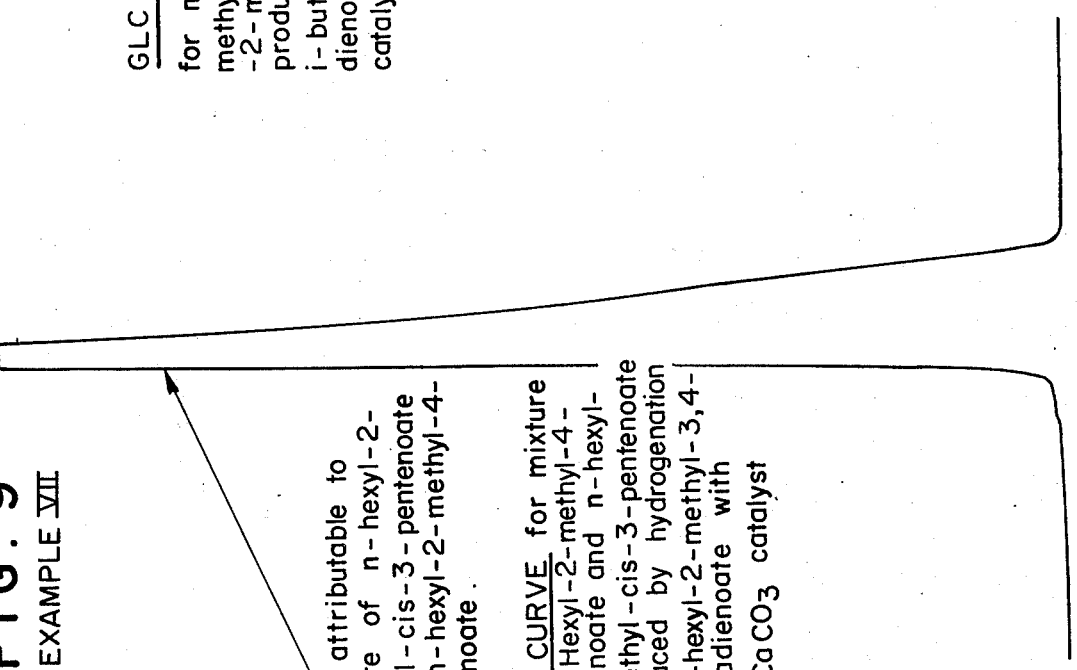

EXAMPLE VIII

NMR SPECTRUM for Isobutyl-2-methyl-3,4-pentadienoate

EXAMPLE VIII

INFRA RED SPECTRUM for Isobutyl-2-methyl-3,4-pentadienoate

PROCESS FOR PREPARING ONE OR MORE ALKYL-2-METHYL PENTENOATES BY MEANS OF HYDROGENATION OF ONE OR MORE ALKYL-2-METHYL-3,4-PENTADIENOATES

BACKGROUND OF THE INVENTION

This invention relates to methods for producing (i) isomeric mixtures containing greater than 60% cis-2-methyl-3-pentenoic acid or lower alkyl esters thereof, and/or (ii) 2-methyl-4-pentenoic acid or lower alkyl esters thereof and/or (iii) 2-methyl-pentanoic acid or lower alkyl esters thereof, by means of hydrogenation of 2-methyl-3,4-pentadienoic acid esters and, if desired, hydrolysis thereof.

There has been considerable work performed relating to efforts to obtain inexpensive substances which can be used to impart (or enhance) flavors to (or in) various consumable materials. These substances are used to diminish the use of natural materials, some of which may be in short supply and to provide more uniform properties in the finished product. Sweet, fruity, strawberry, winey-cognac, butter-like, rum-like, butterscotch, cooked strawberry jam, pineapple-like, pear, green and applie-like aromas as well as sweet, strawberry, nutty-coconut, fatty, butter-like, rum-like, butterscotch-like tastes are particularly desirable for many uses in foodstuff flavors, medicinal product flavors and/or chewing gum flavors. Green, sweet, sharp, strawberry, fruity, strawberry-like, sweet, cheesy, animal, berry, green, pear and banana notes are desirable in perfume compositions. Notes having Turkish-like characteristics as well as aromatic, sweet, bitter, woody, smokey, sour, fruity and green notes are desirable in tobacco flavoring compositions.

U.S. Pat. No. 3,499,769 issued on Mar. 10, 1970 discloses processes for imparting a fresh fruity flavor (particularly strawberry flavor) to foods by adding a small amount of 2-methyl-2-pentenoic acid to the foodstuff.

Arctander, "Perfume and Flavor Chemicals", 1969 discloses the use in perfume compositions and flavors of 4-pentenoic acid, thus:

"... only rarely used in perfume compositions mainly on fruity bases and certain artificial essential oils.

It finds use in flavors on account of its sour-caramellic taste, pleasant at levels below 10 ppm, and including an almost sweet aftertaste. Higher concentrations have acrid taste and repulsively acid odor, pungent and irritating.

Traces, equivalent to 1 to 5 ppm, are used in imitation butter flavor and in various fruit flavor complexes, e.g., apple, pineapple, apricot and strawberry."

at Volume II, No. 2452. Arctander also discloses the use of trans-2-methyl-2-butenoic acid (tiglic acid) at Vol. II, No. 2949 in perfumery:

"Spicy-rooty, sweet-sour herbaceous odor of moderate tenacity."

and the use of 2-methyl-cis-2-butenoic acid (angelic acid) and alkyl esters thereof in perfumes and flavors at Vol. I, No. 238.

Rossi and Ingrosse, Chem.Abstra. 69, 95851 (g) (Abstract of Gazz.Chim.Ital. 98(7), 866–83 (1968) ) discloses the preparation of 2-methyl-4-pentenoic acid by reacting 3-chloropropene-1 with 1,1-dicarboethoxyethane.

De Moura Campos and de Amarat, Chem.Abstr. 63: 4159(e) (Abstract of J.Arch.Pharm. 298(2), 92–100 (1965) discloses the preparation of 2-methyl-4-pentenoic acid by the following reaction sequence:

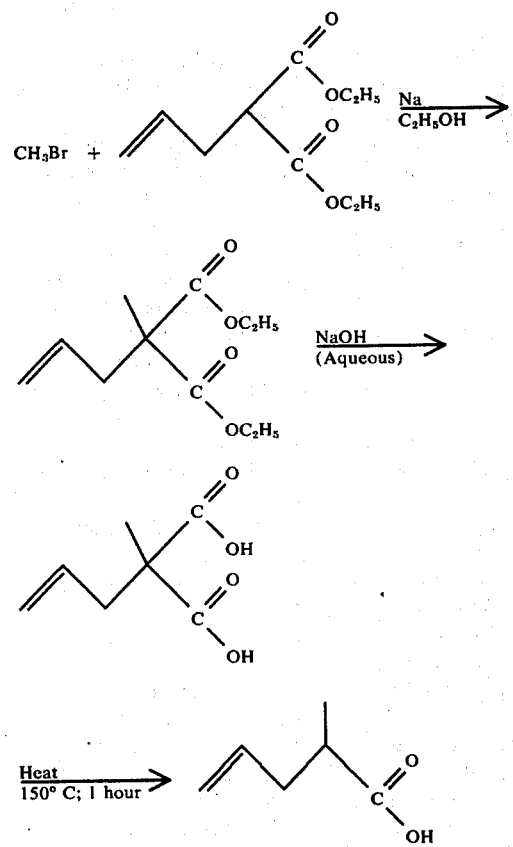

Trace and Gurante, Chem.Abstr. 55:14324(i) Abstract of Rend.Inst.Lombardo Sci. Pt.I,Classe Sci. Mat. e Nat., 94A, 309–330 (1960) discloses a process for preparing 2-methyl-4-pentenoic acid by reacting 2-cyclopropyl -propionic acid with HBr.

Adler and Brachel Chem.Abstr. 57: 2042(d) (Abstract of Ann. 651, 141–53 (1962) sets forth a process for giving 12% yields of methyl-2-methyl-4-pentenoate by means of the following reaction:

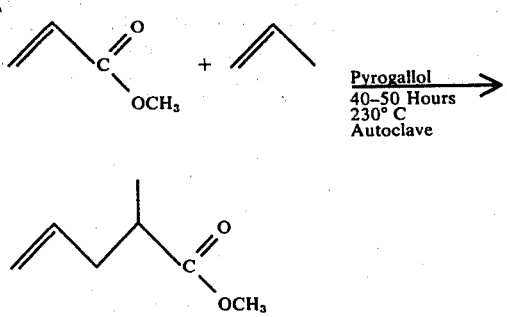

In the prior art, a number of methods are known for producing the lower alkyl esters of 2-methyl-3-pentenoic acid but either they do not produce isomeric mixtures having desirable aroma and taste impressions or they are not considered to be economical:

1. Chem. Abstracts 47:4318i — Colonge, J. Domensh, R.-Bull.Soc.Chim.Franc 634-7(1952) — By esterification of acid (Trans ethyl ether).
2. Chem. Abstracts 59:2795a — McGreer, D. E. et al., Can.J.Chem. 41, 726–31 (1963) Trans methyl ester by pyrolysis of 3,5-dimethyl-3-carbomethoxy Δ¹ -pyrazoline.
3. Chem. Abstracts 61:14522c — Tsuji, J. et al., J.Am.Chem.Soc. 86 (20) 4350-3 (1964) —allylic compounds with PdCl₂.
4. Chem. Abstracts 63:P501c — Fr. Pat. No. 1,389,856, Feb. 19, 1965 (To Toyo Rayon Co.) Synthesis of Trans beta, alpha- unsaturated carboxylic esters.
5. Chem. Abstracts 63:6851c — Brewis, S. and Hughes, P. R. — Chem. Commun. (8) 157–8 (1965). Trans esters from conjugated dienes in the presence of carbon monoxide at 1000 atm.
6. Chem. Abstracts 21388f — Bordenca, C. and Marsico, W. E. Tetrahedron Lett. (16), 1541–3 (1967). Trans esters by carbonylation of piperylene in the presence of PdCl₂.
7. Chem. Abstracts 75:75686k — Felkin, H. et al — Ann.Chim. (Paris) 6(1), 17–26 (1971) Cis Ester by reaction of allylmagnesium bromide with acetone.
8. Chem. Abstracts 75:109792j — Hosaka, S. and Tsuji, J. — Tetrahedron 27(16) 3821-9 (1971) Trans ester by carbonylation of piperylene in the presence of PdCl₂.

Although the prior art contains no suggestion for producing such materials by means of hydrogenation of esters of 2-methyl-3,4-pentadienoic acid, the following references do teach reduction of allenic dienes by means of hydrogenation:

1. U.S. Application for Letters Patent Ser. No. 490,717 filed on July 22, 1974 discloses a process for preparing isomer mixtures containing major proportions of 2-methyl-cis-3-pentenoic acid by first reacting methyl acetylene with a methyl magnesium halide to form a methyl acetylene magnesium halide Grignard reagent; then reacting the methyl acetylene magnesium halide Grignard reagent with acetaldehyde to form a 3-pentyn-2-ol magnesium halide salt; then hydrolyzing the magnesium halide salt to form 3-pentyn-2-ol; then halogenating the 3-pentyn-2-ol to form a 4-halo-2-pentyne; then reacting magnesium with the 4-halo-2-pentyne to produce a 4-magnesium halo-2-pentyne Grignard reagent; then reacting the 4-magnesium halo-2-pentyne Grignard reagent with carbon dioxide to form a magnesium halo-carboxylate salt mixture of compound having the structures:

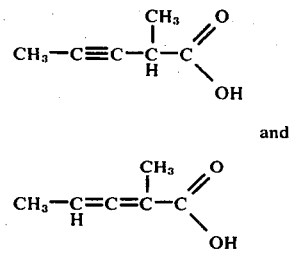

and

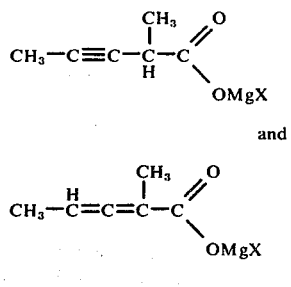

(wherein X is halogen); the hydrolyzing the magnesium halo-carboxylate salt mixture to form a mixture of carboxylic acids having the structures:

then hydrogenating the aforementioned mixture of carboxylic acids to form a mixture containing 80% cis-2-methyl-3-pentenoic acid and 20% of 2-methyl-2-pentenoic acid.

2. Eglinton et al., J.Chem.Soc. (1954) 3197 discloses the reduction of ethyl-2,3-butadienoate to ethyl-3-ethoxy-2-butenoate using sodium ethylate; as well as the partial catalytic hydrogenation of 2,3-butadienoic acid in the presence of 1.5% palladium on calcium carbonate to produce "essentially pure" cis-crotonic acid, according to the following reaction:

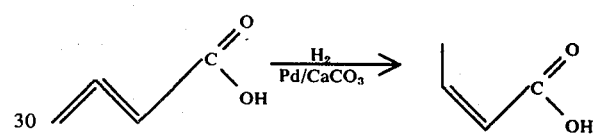

3. Bhagwat and Devaprabhakara, Tetrahedron Letters No. 15, pp 1391 – 1392, 1972 ("Selective Hydrogenation of Allenes with Chlorotris (triphenylphosphine) Rhodium Catalyst") discloses the hydrogenation of 1,2,6-cyclononatriene to form cis, cis-1,5-cyclononadiene.

4. Moore, J.Am.Chem.Soc. (84) 3788 discloses the hydrogenation of 1,2-cyclodecadiene using a 10% Pd on charcoal catalyst to produce 17–32% trans-cyclodecene.

5. Meyer and Burwell, J.Am.Chem.Soc. (85) 2881, Oct. 5, 1963 discloses the hydrogenation of 1,2-butadiene using a Pd on alumina catalyst to produce a mixture containing 53% cis-2-butene, 7% trans-2-butene and 40% 1-butene.

6. Rieche et al., Brennstoff Chem. 42, 177 (1961) discloses the liquid phase hydrogenation of 1,2-butadiene using a Pd-BaSO₄ catalyst to yield 44.5% 1-butene; 3.3% trans-2-butene and 52.2% cis-2-butene.

7. Hennien and Sheehan, J.Am.Chem.Soc. 71, 1964 (June, 1949) discloses hydrogenation over a Raney nickel catalyst of 1,2-hexadiene to "produce a mixture of 1- and 2-hexenes in which the latter appear to dominate".

8. Hennion and DiGiovanna, J.Org.Chem. 30, 3696 (Nov. 1965) discloses the hydrogenation over a Raney-nickel catalyst of quaternary ammonium salts according to the following reaction:

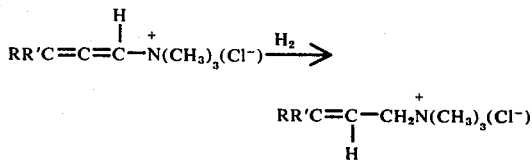

to yield "a mixture of two possible geometric isomers".

9. Crombie et al., Tetrahedron Letters No. 44, pp. 4297–4302, 1967 ("The Stereochemistry of the Palladium-Catalysed Hydrogenation of Allenes") discloses in Ex. 12 hydrogenation of methyl-2-methyl-3,4-butadienoate over a 5% Pd on BaSO₄ catalyst to yield:

7% trans-methyl-2-methyl-2-butenoate;
87% cis-methyl-2-methyl-2-butenoate;
2% "saturated material"; and
4% methyl-2-methyl-3-butenoate according to the following reaction:

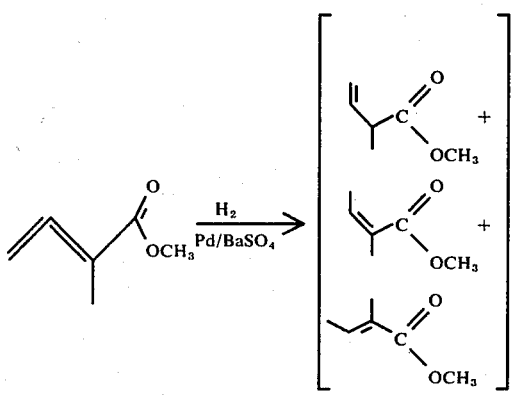

The foregoing prior art does not give rise to any logical prediction of the outcome of carrying out the process of the instant invention.

THE INVENTION

This invention relates to methods for producing one or more alkyl-2-methyl pentenoates having the generic structure:

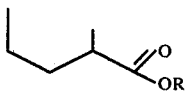

(wherein R is $C_1$–$C_6$ alkyl and one of the dashed lines is a carbon-carbon pi bond) such as alkyl-2-methyl-4-pentenoates or alkyl-2-methyl-cis-3-pentenoates and their corresponding carboxylic acids having the generic structure:

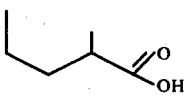

comprising the steps of:

i. Contacting with hydrogen gas one or more alkyl-2-methyl-3,4-pentadienoates having the structure:

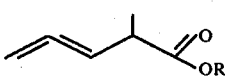

in the presence of a hydrogenation catalyst which may be either of:
a. Raney Nickel;
b. Palladium on carbon; or c. Palladium on calcium carbonate (Lindlar catalyst) at a temperature in the range of from about 10° C up to about 100° C; a hydrogen pressure in the range of from about 5 psig up to about 80 psig, the concentration of said catalyst based on weight of the starting material, the alkyl-2-methyl-3,4-pentadienoate, being from about 0.1% up to about 10%;

ii. Recovering a chemical composition from the reaction mass which contains at least 60% by weight of one or more alkyl-2-methyl-cis-3-pentenoates having the structure:

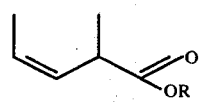

optionally, (iii) separating the ingredients of the resulting chemical composition to obtain such materials as highly refined ethyl-2-methyl-cis-3-pentenoate or ethyl-2-methyl-4-pentenoate; and/or optionally, (iv) forming one or more carboxylic acids by means of admixing the resulting chemical composition with a basic hydrolysis agent which may be either an aqueous solution of alkali metal hydroxide, or an alcoholic solution of an alkali metal hydroxide; and/or optionally, (v) re-esterifying the resulting carboxylic acid by means of reacting same with an esterifying agent such as an alkanol in the presence of a protonic acid catalyst.

Solid and liquid foodstuff, medicinal product, chewing gum and flavoring compositions having sweet, fruity, strawberry, winey-cognac, butter-like, rum-like, butterscotch-like aromas and sweet, strawberry, nutty-coconut, fatty, butter-like, rum-like and butterscotch-like taste notes; and perfume compositions having green, sharp, strawberry notes; as well as tobacco flavoring compositions capable of imparting a turkish-like character to tobacco and having aromatic, sweet, bitter, woody and smokey notes may be provided by the utilization of isomer mixtures containing more than 60% cis-2-methyl-3-pentenoic acid produced according to the process of our invention.

Solid and liquid foodstuff, medicinal product, chewing gum and flavoring compositions having sweet, fruity, strawberry, winey-cognac, pineapple-like, pear, green, and apple-like aromas and tastes, with cooked strawberry jam undertones; perfume compositions having fruity, strawberry-like, sweet, cheesy, animal, berry, green, pear and banana notes; as well as tobacco flavoring compositions capable of imparting a Turkish-like character to tobacco, and having aromatic, sweet, sour, bitter, fruity, green and strawberry notes may be provided by the utilization of the 2-methyl-4-pentenoic acids and $C_1$–$C_6$ alkyl esters thereof having the general formula:

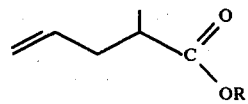

produced according to the process of our invention or (wherein R is hydrogen, one of $C_1$–$C_6$ alkyl) in foodstuffs, perfume compositions, perfumed articles, colognes and tobaccos as well as tobacco substitutes.

Solid and liquid foodstuff, medicinal product, chewing gum and flavoring compositions having sweet, fruity, fresh, berry, pineapple, green, herbaceous, strawberry and pear-like aromas and fruity, berry, woody, green, pear taste notes; and perfume compositions having fruity, peppery, woody, green, herbaceous, strawberry and chamomile notes, as well as tobacco flavoring compositions capable of imparting a "Turkish-like" character to tobacco and having aromatic, sweet, and bitter notes may be provided by the utilization of alkyl esters of 2-methyl-cis-3-pentenoic acid and isomer mixtures of alkyl-2-methyl-3-pentenoates containing greater than 60% cis isomer having the generic formula:

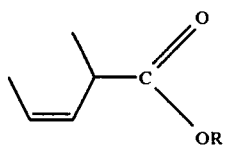

wherein R is $C_1$–$C_6$ alkyl produced according to the processes of our invention.

The term "cis-alkyl-2-methyl-3-pentenoate", as well as the structure:

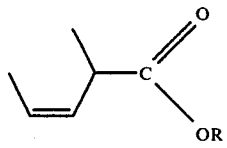

is intended herein to cover one or both stereoisomers of such material, to wit the "cis" stereoisomer having the structure:

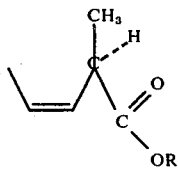

as well as the cis stereoisomer having the structure:

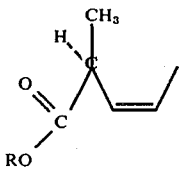

wherein R is $C_1$–$C_6$ lower alkyl.

More specifically, the process of our invention involves the steps of:

a. First reacting 1,1,1-trialkoxy propane (such as 1,1,1-triethoxy propane, or 1,1,1-trihexyloxy propane) with 2-propynol-1 in the presence of a propionic acid catalyst thereby providing the alkyl-2-methyl-3,4-pentadienoate starting material. The reaction temperature range is 120°–180° C with a range of 145°–150° C being preferred. The mole ratios of reactants preferred is 1:1 with a slight excess of either reactant being permissible. A large excess of 2-propynol-1 is undesirable, and a large excess of the trialkoxy propane is uneconomical. The percentage of propionic acid catalyst may vary from 1 up to 3%, but a 2% concentration of catalyst is preferred. Since the reaction temperature is in the range of 120°–180° C, the reaction takes place under higher pressures, e.g. 30–100 psig and this requires the use of an autoclave. The reaction time is inversely dependent on the temperature of reaction. Thus, for example, where the temperature range of reaction is 150°–160° C, the reaction time is approximately 3 hours. The length of reaction time varies between 2 and 6 hours, and a reaction time of 3–4 hours is preferred. The reaction product, the alkyl-2-methyl-3,4-pentadienoate, is then "worked up" and this work up operation is performed by first, if necessary, destroying the excess trialkyl orthopropionate reactant by washing with 5% hydrochloric acid solution. The acid is then neutralized by use of a sodium bicarbonate wash, and the reaction mass is then fractionally distilled.

b. The resulting alkyl-2-methyl-3,4-pentadienoate starting material is then reacted with hydrogen in the presence of a Raney nickel catalyst, or a palladium-on-carbon catalyst, or a "Lindlar" catalyst (palladium-on-calcium carbonate). The percentage of palladium in the palladium on carbon catalyst or in the palladium on calcium carbonate catalyst varies from about 2% up to about 7% with a percentage of palladium in the palladium on-carbon catalyst or in the palladium on calcium carbonate catalyst being preferred to be 5%. The temperature of reaction for this hydrogenation may vary from about 10° C up to about 100° C with a preferred reaction temperature of 25°–35° C. Since the reaction is exothermic, it is usually necessary to provide external cooling to the reaction mass during the course of the reaction. The pressure of hydrogen over the reaction mass may vary from about 5 psig up to about 100 psig, with the most preferred pressure being 20 psig. Pressures greater than 150 psig will give rise to greater amounts of the saturated ester. The hydrogenation reaction may be carried out in the presence of or in the absence of a solvent. When a solvent is used, it is required that it be an inert (non-reactive) solvent such as isopropyl alcohol, hexane or ethanol, with the alkyl moiety of the alcohol solvent being the same as the alkyl moiety of the alkoxy group of the ester being hydrogenated. If a solvent is used, it is preferred that the mole ratio of solvent:hydrogenated ester be approximately 1:1. Where a palladium-containing catalyst is used, the percentage of catalyst in the reaction mass may vary from 0.125% up to about 2.0% with a percentage of catalyst of about 0.25% being preferred. Where a Raney-nickel catalyst is used, the percentage of catalyst in the reaction mass may vary from about 3% up to about 10% with a percentage of catalyst of about 5% being preferred. The hydrogenation reaction produces mixtures including alkyl-2-methyl-cis-3-pentenoate, alkyl-2-methyl-4-pentenoate and alkyl-2-methyl pentanoate, all mixtures containing at least 60% alkyl-2-methyl-cis-3-pentenoate. As a result, the alkyl-2-methyl-cis-3-pentenoate may, if desired, be separated and refined by means of fractional distillation where the only other hydrogenation product is the alkyl-2-methyl pentanoate (where an alkyl-2-methyl-4-pentenoate is one of the hydrogenation products, the reaction product may still be enriched with respect to the alkyl-2-methyl-cis-3-pentenoate by means of fractional distillation); or the mixtures resulting may be used as such for their organoleptic properties as perfume compositions or tobacco flavoring adjuvants, or as flavor adjuvants or enhancer for use in foodstuffs, medicinal products or chewing gums. Where the catalyst used is a Lindlar catalyst (Palladium on calcium carbonate) a mixture of alkyl-2-methyl-cis-3-pentenoate and alkyl-2-methyl-4-pentenoate is produced. Where the catalyst used is palladium-on-carbon rather than palladium-on-calcium carbonate, a mixture of alkyl-2-methyl-cis-3-pentenoate, alkyl-2-methyl-4-pentenoate and alkyl-2-methyl-pentenoate is formed which may be used as such for its organoleptic properties as a flavor adjuvant or enhancer for foodstuffs, tobaccos, chewing gums and medicinal products or as a perfume composition or perfumed article adjuvant. Where the catalyst used in Raney nickel, rather than palladium-on-calcium carbonate, initially produced is a mixture of alkyl-2-methyl-cis-3-pentenoate, alkyl-2-methyl-4-pentenoate and alkyl-2-methyl pentenoate with the percentage of alkyl-2-methyl-cis-3-pentenoate being greater than 50% by weight of the total reaction product produced. As the hydrogenation proceeds, however, the percentage of alkyl-2-methyl-4-pentenoate diminishes to 0 and the percentage of alkyl-2-methyl pentanoate increases, with the quantity of alkyl-2-methyl-cis-3-pentenoate remaining about the same. In any event, at the end of the hydrogenation reaction, the reaction mass is filtered in order to separate catalyst from liquid phase desired product, and the filtrate is distilled using a fractional distillation column operated under vacuum.

c. If desired, the resulting alkyl-2-methyl-4-pentenoate (and if desired other esters which may not have been separated therefrom after the hydrogenation reaction) may be converted into the corresponding carboxylic acids by the standard saponification and acidification reactions. The saponification is preferably carried out using strong aqueous base, e.g., 50% aqueous sodium hydroxide or 50% aqueous potassium hydroxide admixed with methanol. After acidification of the resulting salt of the carboxylic acid (e.g., the sodium or potassium salt) is acidified using mineral acid (e.g., a 6 molar aqueous hydrochloric acid), and the carboxylic acid is extracted from the aqueous phase using an organic solvent such as toluene. The organic solvent is then stripped from the acid, and the acid is fractionally distilled. The resulting acid may be used as such or it may, if desired, be esterified with an alkanol to form another ester of said carboxylic acid.

d. If desired, the alkyl-2-methyl pentenoate ester(s) produced as set forth in (b) supra, may be converted into other esters, such as a $C_3$, $C_4$, $C_5$ or $C_6$ ester of 2-methyl-4-pentenoic acid or 2-methyl-3-pentenoic acid, as the case may be, by reaction with a $C_3$, $C_4$, $C_5$ or $C_6$ alkanol in the presence of a protonic acid catalyst at a temperature in the range of 100°–170° C. The preferred temperature depends upon the particular alkanol used; e.g., about 110° C in the case of isobutyl alcohol; and 140°–150° C in the case of n-hexanol. The preferred catalyst is paratoluene sulfonic acid.

The foregoing series of reactions may be illustrated as follows:

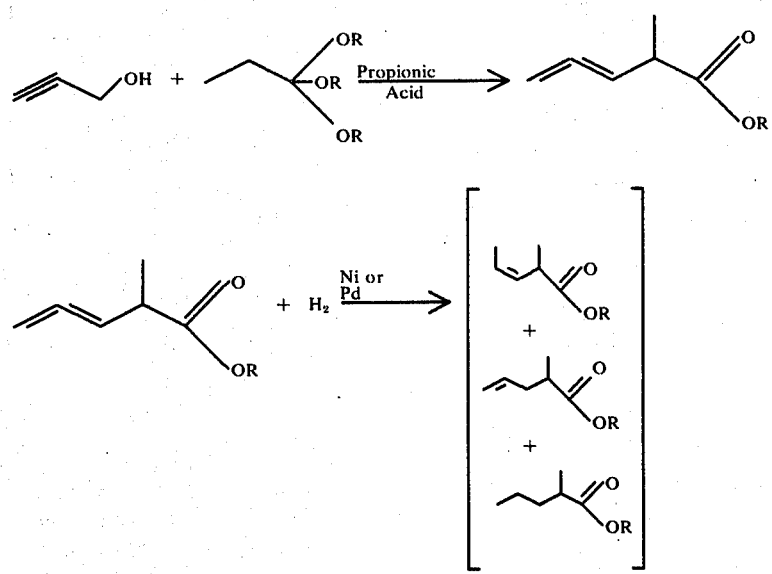

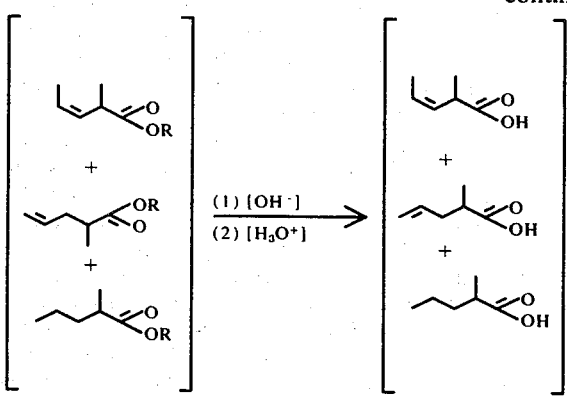

Examples of reaction products and organoleptic characteristics of such reaction products, are set forth in the following table:

| Reaction Product | Organoleptic Properties |
|---|---|
| Ethyl-2-methyl-cis-3-pentenoate | Fruity, fresh, pineapple, strawberry aroma and sweet, fruity, pineapple, strawberry, mellon-green taste at 1 ppm. Also, a fruity, green, strawberry fragrance note with a chamomile nuance. |
| Isopropyl-2-methyl-cis-3-pentenoate | A fruity, characteristic strawberry taste and a sweet, astringent after-taste at 5 ppm; and a fruity, herbaceous fragrance note. |
| Isobutyl-2-methyl-cis-3-pentenoate | Characteristic sweet, strawberry taste, with lasting strawberry after-taste at 5 ppm; at 10 ppm, characteristic sweeter strawberry taste with a lasting sweet strawberry after taste. Also, a fruity, woody fragrance note. |
| n-Hexyl-2-methyl-cis-3-pentenoate | A pear, strawberry, fruity, aroma and a sweet, strawberry, pear, fruity taste at 2 ppm. In addition, fruity, peppery, chamomile and floral fragrance notes. |
| Ethyl-2-methyl-4-pentenoate | (i) Food Flavor: At 0.05 ppm, fresh, sweet, fruity; at 0.1 ppm, very pleasant strawberry, winey; at 0.2 ppm, wine, pineapple-like; at 0.5 ppm, strawberry, apple, fruity; at 1 ppm, green, fruity; at 2 ppm, green, apple. (ii) Fragrance: Green, sweet notes; fruity and strawberry notes. (iii) Tobacco Flavor: Sweet, fruity, strawberry-like and slightly green aroma. At 100 ppm and 200 ppm. on smoking, more aromatic, less harsh, Turkish tobacco-like. |
| 2-Methyl-4-pentenoic acid | (i) Food Flavor: Cooked strawberry jam type aroma and taste at 10 ppm. (ii) Fragrance: cheesy, slight animal, sweet, berry notes. (iii) Tobacco Flavor: Pungent, sweet, fruity, sour and green notes. At 100 ppm and 200 ppm on smoking, sweeter and Oriental, Turkish-like aroma. |
| Isobutyl-2-methyl-4-pentenoate | (i) Food Flavor: At 5 ppm, fruity, pineapple and strawberry aroma and fruity, pineapple, strawberry and sweet taste. (ii) Fragrance: A green, sweet, fruity and berry note. |
| n-Hexyl-2-methyl-4-pentenoate | (i) Food Flavor: At 5 ppm, pear and green aroma and taste notes. (ii) Fragrance: A green, floral, slight fruity-apple, pear and banana note. |

When the 2-methyl pentenoic acid or alkyl-2-methyl pentenoate product(s) or mixture(s) produced by the process of our invention are used as food flavor adjuvants, or chewing gum flavor adjuvants or medicinal product flavor adjuvants, the nature of the co-ingredients included with the said 2-methyl pentenoic acid or alkyl-2-methyl pentenoate in formulating the product composition will also serve to alter the organoleptic characteristics of the ultimate foodstuff or medicinal product or chewing gum treated therewith.

As used herein in regard to flavors, the term "alter" in its various forms means "supplying" or imparting flavor character or note to otherwise bland, relatively tasteless substances or augmenting the existing flavor characteristic were a natural flavor is deficient in some regard or supplementing the existing flavor impression to modify its quality, character or taste.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible materials which have medicinal value such as cough syrups, cough drops, aspirin, and chewable medicinal tablets.

The term "chewing gum" is intended herein to mean a composition which comprises a substantially water-insoluble, chewable, plastic gum base such as chicle, or substitutes therefor, including jelutong guttakay rubber or certain comestible natural or synthetic resins or waxes. Incorporated with the gum base and an admixture therewith may be plasticizers or softening agents, e.g., glycerine; and a flavoring composition which incorporates the alkyl-2-methylpentenoate or 2-methyl pentenoic acid produced by the process of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious, nothing particularly critical resides in the selection thereof. Accordingly, such materials which may, in general, be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2 and 3 tertiary butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agaragar; carrageenan; cellulose and cellulose derivatives, such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono-and diglycerides of fatty acids, skim milk powder, hexoses, pentoses, disaccharides, e.g., sucrose, corn syrup solids and the like.

Surface active agents include emulsifying agents, e.g., fatty acids such as capric acid, caprylic acid, palmitic acid, myristic acid and the like, mono-and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like; firming agents such as aluminum sodium sulfate, calcium chloride and calcium gluconate; texturizers; anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic-acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethylacrolein, n-hexanal, 2-hexenal, cis-3-hexenal, 2-heptanone, 4-(p-hydroxyphenyl)-2-butanone, alpha-ionone, beta-ionone, methyl-3-butanone, 2-pentanone, 2-pentenal and propanal; alcohols, such as 1-butanal, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha terpineol, cis-terpineol hydrate; esters, such as butyl acetate, ethyl acetate, ethyl acetoacetate, ethyl benzoate, ethyl butyrate, ethyl capronate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl capronate, methyl isobutyrate, alpha-methylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmine absolute, rose absolute, orris absolute, lemon essential oil, bulgarian rose, yara yara, natural raspberry oil and vanilla; lactones; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, be capable of providing an environment in which the alkyl-2-methyl pentenoate or 2-methyl pentenoic acid product or mixture produced by the process of our invention can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of alkyl-2-methyl pentenoate or 2-methyl pentenoic acid produced by the process of our invention employed in a particular instance can vary over a relatively wide range whereby its desired organoleptic effects (having reference to the nature of the product) are achieved. Thus, correspondingly greater amounts would be necessary in those instances wherein the ultimate food composition to be flavored is relatively bland to the taste, whereas relatively minor quantities may suffice for purposes of enhancing a composition merely deficient in natural flavor or aroma. Thus, the primary requirement is that the amount selected should be "effective", i.e., sufficient to alter the organoleptic characteristics of the parent composition, whether foodstuff per se or flavoring composition. Thus, the use of insufficient quantities of alkyl-2-methyl pentenoate or 2-methyl pentenoic acid will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of alkyl-2-methyl pentenoate or 2-methyl pentenoic acids ranging from a small but effective amount, e.g., 0.10 parts per million up to about 50 parts per million by weight based on total composition are suitable. Concentrations in excess of the maximum quantity stated are not normally recommended since they fail to provide commensurate enhancement of organoleptic properties. In those instances wherein the alkyl-2-methyl pentenoate or 2-methyl pentenoic acid is added to the foodstuff as an integral component of a flavoring composition, it is of course essential that the total quantity of flavoring composition employed be sufficient to yield an effective alkyl-2-methyl pentenoate or 2-methyl pentenoic acid concentration in the foodstuff product.

Food flavoring compositions prepared in accordance with the present invention preferably contain the alkyl-2-methyl pentenoate or 2-methyl pentenoic acid in concentrations ranging from about 0.05% up to about 10% by weight based on the total weight of said flavoring composition.

The compositions described herein can be prepared according to conventional techniques well known, as typified by cake batters and vegetable juices, can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the alkyl-2-methyl pentenoate or 2-methyl pentenoic acid with, for example, gum arabic, gum tragacanth, carrageenan and the like, and thereafter spray-drying the resultant mixture whereby to obtain the particular solid product. Pre-prepared flavor mixed in powder form, e.g., a strawberry-flavored powder mix or a raspberry-flavored powder mix are obtained by mixing the dried solid components, e.g., starch, sugar and the like and the alkyl-2-methyl pentenoate or 2-methyl pentenoic acid in a dry blender until the requisite degree of uniformity is achieved.

It is presently preferred to combine with the alkyl-2-methyl pentenoate or 2-methyl pentenoic acid the following adjuvants:
Parahydroxy benzyl acetone;
Vanillin;
Maltol;
Ethyl-3-methyl-3-phenyl glycidate;
Benzyl acetate;
Ethyl butyrate;
Methyl cinnamate;
Methyl anthranilate;
Alpha-ionone;
Gamma-undecalactone;
Diacetyl;
Anethole;
Cis-3-hexenol;
2-(4-hydroxy-4-methyl pentyl) norbornadiene (prepared according to Example II of application for U.S. Letters Pat. Ser. No. 461,703 filed on Apr. 17, 1974);
Beta-ionone;
Isobutyl acetate;
Dimethyl sulfide;
Acetic acid;
Acetaldehyde;
4-(2,6,6-trimethyl-1,3-cyclohexadiene-1-yl)-2-butanone (prepared according to Example XVI of application for U.S. Letters Pat. Ser. No. 386,320 filed on Aug. 7, 1973);
4-(6,6-dimethyl-2-methylene-3-cyclohexen-1-yl)-2-butanone (prepared according to Example XVI of application for U.S. Pat. No. 386,320 filed on Aug. 7, 1973);
Geraniol;
Ethyl pelargonate;
Isoamyl acetate;
Naphthyl ethyl ether;
Ethyl acetate;
Isoamyl butyrate;
2-Methyl-2-pentenoic acid;
2-Methyl-3-pentenoic acid;
Elemecine (4-allyl-1,2,6-trimethoxy benzene);
Isoelemecine (4-(1-propenyl)-1,2,6-trimethoxy benzene)

The alkyl-2-methyl pentenoate or 2-methyl pentenoic acid produced according to the process of our invention can also be used to improve and augment the organoleptic properties of tobacco and tobacco products. Thus, the said alkyl-2-methyl pentenoate or 2-methyl pentenoic acid will impart a Turkish-like character to tobacco (in smoke flavor) when used at levels of from 50 parts per million up to 500 parts per million based on the dry weight of the tobacco. "Tobacco" as used herein, includes natural tobaccos such as burley, Turkish tobacco, Maryland tobacco, tobacco-like products such as reconstituted tobacco or homogenized tobacco and tobacco substitutes intended to replace natural tobacco such as various vegetable leaves, for example, lettuce, cabbage leaves and the like.

One or more of the alkyl-2-methyl pentenoates or 2-methyl pentenoic acids produced according to the process of our invention and an auxiliary perfume ingredient, including, for example, one or more alcohols, aldehydes, nitriles, esters, cyclic esters and natural essential oils, may be admixed so that the combined odors of the individual components produce a pleasant and desired fragrance, particularly and preferably in strawberry or raspberry fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, each of the individual components will contribute its particular olfactory characteristics, but the over-all effect of the perfume composition will be the sum of the effects of each of the ingredients. Thus one or more of the alkyl-2-methyl pentenoates or 2-methyl pentenoic acids of our invention can be used to alter the aroma characteristics of a perfume composition, for example, by utilizing or moderating the olfactory reaction contributed by another ingredient in the composition.

The amount of alkyl-2-methyl pentenoate or 2-methyl pentenoic acid of our invention which will be effective in perfumed articles, perfume compositions or perfumed compositions depends on many factors, including the other ingredients, their amounts and the effects which are desired. It has been found that perfume compositions containing as little as 0.3% of alkyl-2-methyl pentenoate or 2-methyl pentenoic acid, or even less (e.g., 0.05%), can be used to impart a scent odor to soaps, cosmetics, or other products. The amount employed can range up to 100% of the fragrance components and will depend on considerations of cost, nature of the end product, the effect desired on the finished product and the particular fragrance sought.

One or more of the alkyl-2-methyl pentenoates or 2-methyl pentenoic acids produced according to the process of our invention is useful by themselves or in perfume compositions such as an olfactory component in detergents, and soaps; space odorants and deodorants, perfumes, colognes, toilet water, bath preparations, such as bath oils, and bath solids; hair preparations, such as lacquers, brilliantines, pomades and shampoo; cosmetic preparations, such as creams, deodorants, hand lotions and sun screens; powders, such as talcs, dusting powders, face powders and the like. When used as an olfactory component of a perfumed article, as little as 100 parts per million of the alkyl-2-methyl pentenoate or 2-methyl pentenoic acid will suffice to impart a fruity, green, strawberry note with chamomile nuances; or fruity herbaceous notes or fruity, peppery chamomile, floral notes, all of which are key odor characteristics of strawberry and/or raspberry perfume formulations. Generally, no more than 2.0% of the alkyl-2-methyl pentenoate or 2-methyl pentenoic acid, based on the ultimate end product, is required in the perfume composition.

In addition, the perfumed article, perfume composition, perfumed composition or fragrance composition of our invention can contain a vehicle or carrier for the alkyl-2-methyl pentenoate or 2-methyl pentenoic acid. The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

It will thus be apparent that one or more of the alkyl-2-methyl pentenoate or 2-methyl pentenoic acid produced according to the process of our invention can be utilized to alter the sensory properties, particularly organoleptic properties, such as flavor and/or fragrance of a wide variety of consumable materials.

The following Examples I–X are given to illustrate embodiments of the invention as it is presently preferred to practice it. Examples XI–XXVIII are given to illustrate the usefulness of the products produced according to the process of our invention. It will be understood that these examples are illustrative, and the invention is not to be considered as restricted thereto except as indicated in the appended claims. All parts and percentages set forth herein are by weight unless otherwise specified.

EXAMPLE I

Preparation of Ethyl-2-Methyl-3,4-Pentadienoate

Reaction:

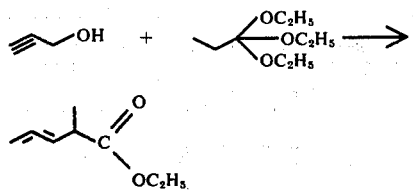

Into a 2 liter autoclave, the following materials are placed:

| Ingredient | Amount |
| --- | --- |
| Triethyl orthopropionate | 495 grams |
| 2-Propyn-1-ol | 90 grams |
| Propionic acid | 12 grams |

The autoclave is closed and the reaction mass is heated to 150° C. over a period of 50 minutes. The reaction mass is then maintained at a temperature of between 135°–160° C and at a pressure of 20 up to 60 psig for a period of 3 hours. At the end of this 3-hour period, the autoclave is cooled to room temperature and then opened. 12.6 g of sodium bicarbonate is then added to the reaction mass in order to neutralize the propionic acid. 30 g of Primol (see note 1) and 0.1 g of Ionol (see note 2) are added and the resulting reaction product is fractionally distilled at atmospheric pressure to a pot temperature of 129° C. A mixture of ethanol and ethyl propionate is distilled over. Vacuum is then applied to the distillation column and the resultant product, ethyl-2-methyl-3,4-pentadienoate is distilled at a vapor temperature of 65°–69° C at a pressure of 24–33 mm Hg as fractions 5–10 of the following fractions:

| Fraction No. | Vapor Temperature | Liquid Temperature | Pressure (mm Hg) | Weight of Fraction | Reflux Ratio |
| --- | --- | --- | --- | --- | --- |
| 1 | 68 – 72° C | 127 – 87° C | 760 | 174.5 g | 9:1 |
| 2 | 28 – 42 | 86 – 83 | 48 – 50 | 19.4 | 9:1 |
| 3 | 69 | 84 | 45 | 12.6 | 9:1 |
| 4 | 65 | 79 | 34 | 20.1 | 9:1 |
| 5 | 67 | 80 | 33 | 38.9 | 4:1 |
| 6 | 67 | 82 | 33 | 32.5 | 4:1 |
| 7 | 67 | 82 | 33 | 36.8 | 4:1 |
| 8 | 67 | 83 | 33 | 37.2 | 4:1 |
| 9 | 66 | 84 | 24 | 39.8 | 4:1 |
| 10 | 65 | 94 | 24 | 36.9 | 4:1 |
| 11 | 57 | 108 | 10 | 45.5 | 4:1 |
| 12 | 39 | 172 | 2.3 | 14.5 | 4:1 |

The resulting material is confirmed by IR, NMR and mass spectral analyses to have the structure:

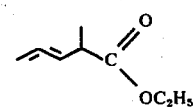

Mass spectral analysis:

Parent peak, then in order of decreasing intensity:

m/e = 140/ 67, 97, 29, 41, 125

Nuclear Magnetic Resonance Analysis:

| ppm | Interpretation | | |
|---|---|---|---|
| 1.26 ppm (t) | CH₃—C—O—C— (=O) | } 6H | |
| 1.28 ppm (d) | CH₃—C—C— (=O) | | |
| 3.10 ppm (m) | =C—CH—C=O | 1H | |
| 4.12 ppm (q) | CH₃—CH₂—O—C— (=O) | 2H | |
| 4.76 ppm (m) | H₂C=C=C— | 2H | |
| 5.40 ppm (m) | C=C=CH | 1H | |

The nuclear magnetic resonance spectrum is set forth in FIG. 1.

Infra Red Analysis:
 Peaks:
 850 cm⁻¹
 1050
 1175
 1225
 1375
 1425
 1730
 1950
 2880
 2925
 2975

Figure 2:
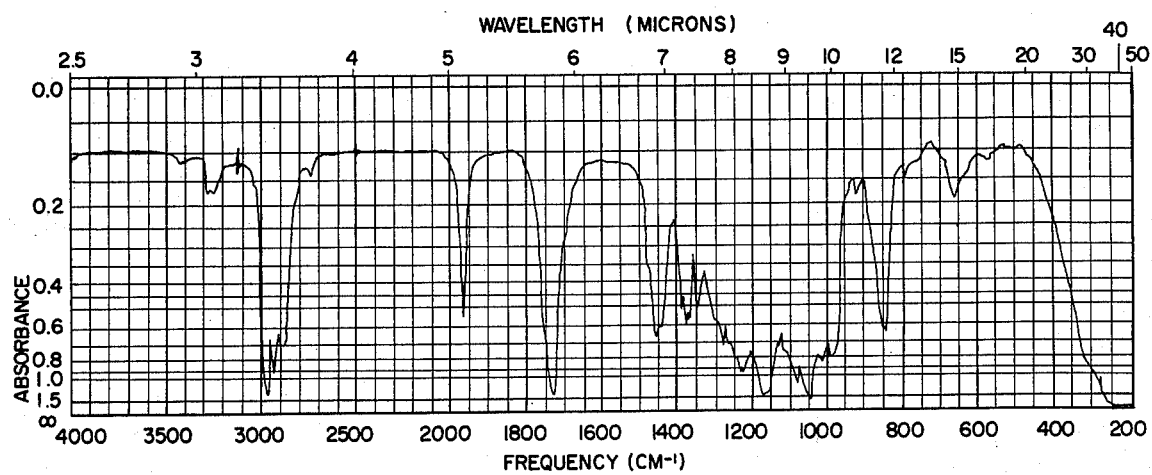

The infra-red spectrum is set forth in FIG. 2.

Note 1: Primol is a registered trademark identifying a hydrocarbon mineral oil produced by Exxon Corp. of Linden, N.J.

Note 2: Ionol is a registered trademark identifying the compound 2,6-di-t-butyl-4-methyl phenol.

EXAMPLE II

Hydrogenation of Ethyl-2-Methyl-3,4-Pentadienoate Using a 5% Palladium on Carbon Catalyst Reaction:

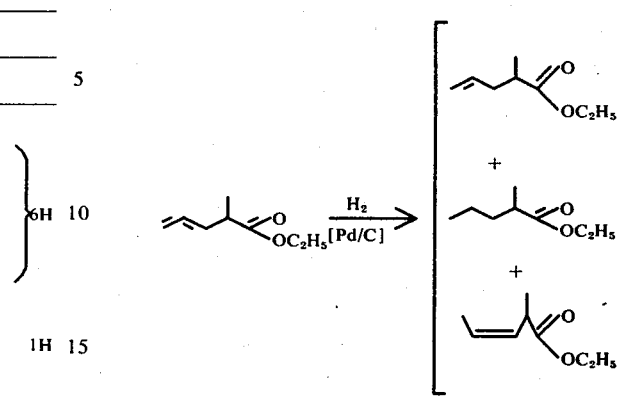

Into a 250 cc Parr Bomb, the following ingredients are placed:

| Ingredient | Amount |
|---|---|
| Ethyl-2-methyl-3,4-pentadienoate produced according to the process of Example I | 25 grams |
| 5% Palladium on carbon | 0.025 grams |

The Parr Bomb is connected by means of pressure tubing to a hydrogen-containing cylinder. The Parr Bomb is then sealed. Hydrogen is introduced from the hydrogen-containing cylinder and maintaining the pressure within the Parr Bomb at 25–50 ppsi. The reaction is maintained at room temperature using external cooling. After a period of 3.5 hours, the Parr Bomb is opened and the contents are filtered. GLC analysis indicates that the reaction is completed. GLC analysis (conditions: 8 foot × ¼ inch carbowax column; column temperature 120° C) indicates weight percentages of the following components:

| Component | Weight Percent |
|---|---|
| Ethyl-2-methyl-cis-3-pentenoate | 65.7% |
| Ethyl-2-methyl-4-pentenoate | 14.3% |
| Ethyl-2-methyl pentanoate | 19.9% |

The GLC spectrum is illustrated in FIG. 3.

EXAMPLE III

Hydrogenation of Ethyl-2-Methyl-3,4-Pentadienoate Using a Lindlar Catalyst, Thereby Preparing Mixtures of Ethyl-2-Methyl-Cis-3-Pentenoate Reaction:

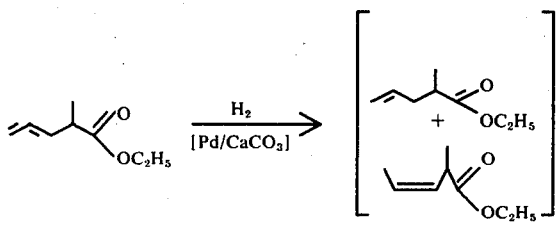

Into a 2-liter autoclave, the following ingredients are placed:

| Ingredient | Quantity |
| --- | --- |
| Ethyl-2-methyl-3,4-pentadienoate produced according to the process of Example I | 577.8 grams |
| 5% Palladium on calcium carbonate catalyst (Lindlar catalyst) | 1.4 grams |

The autoclave is connected by means of pressure tubing to a hydrogen-containing cylinder. The autoclave is then sealed. Hydrogen is introduced into the autoclave from the hydrogen-containing cylinder and maintaining the pressure within the autoclave at 60 pounds per square inch. During the hydrogenation and over a 19-hour period, the reaction mass is maintained at room temperature by means of the application of cooling. At the end of the 19-hour period, the autoclave is opened; and an additional 1.4 grams of Lindlar catalyst is added. The autoclave is then closed and hydrogen is continuously added thereto while stirring the reaction mass over an additional reaction period of 10 hours. At the end of the 10-hour period, the autoclave is opened, and the reaction mass is filtered. An additional 2.8 grams of Lindlar catalyst is then added to the reaction mass which is then again placed in the autoclave with hydrogen being added thereto and pressure being maintained at 60 pounds per square inch gauge. At the end of one and three-quarter hours, GLC analysis indicates that the reaction is completed. The autoclave is then opened and the reaction mass is filtered. The filtered reaction mass is then distilled on a 1 inch × 1 foot Goodloe distillation column after adding thereto 10 grams of Primol (see Note 1) and 0.1 grams of Tonol (see Note 2) yielding the following fractions.

| Fraction No. | Vapor Temp. | Liquid Temp. | (Vacuum (mm Hg) Pressure) | Weight of Fraction | Reflux Ratio |
| --- | --- | --- | --- | --- | --- |
| 1 | 31–33° C | 77–86° C | 200–205 | 18.2 g | 19:1 |
| 2 | 60 | 90 | 200 | 17.0 | 19:1 |
| 3 | 61 | 93 | 200 | 11.0 | 19:1 |
| 4 | 62 | 97 | 200 | 12.6 | 19:1 |
| 5 | 62 | 100 | 200 | 13.6 | 19:1 |
| 6 | 62 | 107 | 200 | 13.5 | 19:1 |
| 7 | 62 | 111 | 200 | 14.3 | 19:1 |
| 8 | 65 | 115 | 200 | 12.5 | 19:1 |
| 9 | 81 | 119 | 200 | 13.1 | 19:1 |
| 10 | 88–110 | 116–117 | 205 | 6.6 | 19:1 |
| 11 | 112 | 117 | 205 | 6.0 | 19:1 |
| 12 | 113 | 117 | 205 | 6.2 | 19:1 |
| 13 | 113 | 118 | 205 | 7.0 | 19:1 |
| 14 | 114 | 118 | 205 | 4.5 | 19:1 |
| 15 | 114 | 118 | 205 | 17.8 | 9:1 |
| 16 | 114 | 118 | 205 | 21.5 | 9:1 |
| 17 | 114 | 118 | 205 | 23.9 | 9:1 |
| 18 | 114 | 118 | 205 | 21.2 | 9:1 |
| 19 | 115 | 120 | 205 | 24.5 | 9:1 |
| 20 | 115 | 120 | 205 | 23.2 | 9:1 |
| 21 | 115 | 120 | 205 | 10.0 | 9:1 |
| 22 | 114–115 | 119–120 | 200–205 | 20.8 | 9:1 |
| 23 | 115 | 121 | 205 | 20.8 | 9:1 |
| 24 | 115 | 121 | 205 | 15.0 | 9:1 |
| 25 | 115 | 122 | 205 | 19.3 | 9:1 |
| 26 | 115 | 124 | 205 | 17.9 | 9:1 |
| 27 | 116 | 125 | 205 | 21.9 | 9:1 |
| 28 | 116 | 128 | 205 | 18.9 | 9:1 |
| 29 | 116 | 131 | 205 | 19.0 | 4:1 |
| 30 | 116 | 144 | 205 | 24.6 | 4:1 |
| 31 | 116 | 160 | 205 | 13.5 | 4:1 |
| 32 | 111 | 200 | 205 | 6.1 | 4:1 |

Fractions 12–31 are bulked.

Fractions 12, 13, 14, 21, 23 and 31 are analyzed using GLC analysis (conditions: 10 foot × ¼ inch Carbowax 20M column programmed at 120°–150° C).

| Fraction No. | Weight of Fraction | Percentage ethyl-2-methyl-cis-3-pentenoate | Percentage ethyl-2-methyl-4-pentenoate |
| --- | --- | --- | --- |
| 12 | 6.2 g | 57.6% | 41.6% |
| 13 | 7.0 g | 59.2% | 38.9% |
| 21 | 10.0 g | 70.9% | 28.7% |
| 23 | 20.8 g | 75.6% | 24.1% |
| 31 | 13.5 g | 93.8% | 4.9% |

The GLC curve for Fraction No. 23 is set forth in FIG. 4.

Analyses:
a. Ethyl-2-methyl-cis-3-pentenoate
  i. Mass Spectral Analysis: Parent Peak; then in decreasing order of intensity: m/e = 142/ 69, 41, 29, 27, 39, 68.
  ii. NMR Analysis:

| ppm | Interpretation | |
|---|---|---|
| 1.18 (d) | | |
| 1.22 (t) | =C—C(CH₃)—C=O ; CH₃—C—O | 6H |
| 1.64 (d) | =C—CH₃ | 3H |
| 3.40 (m) | =C—C(H)—C=O | 1H |
| 4.10 (q) | —CH₂—O—C(=O)— | 2H |
| 5.20 (m) | HC=CH | 2H |

Infrared Analysis:
710, 860, 960, 1020, 1045, 1090, 1140, 1175, 1240, 1325, 1370, 1395, 1450, 1650, 1730, 2880, 2900, 2940, 2980, 3020 cm$^{-1}$ b. Ethyl-2-methyl-4-pentenoate
Mass spectral analysis: Parent peak then in decreasing order of intensity, m/e = 142/69, 41, 29, 27, 39, 68.
NMR Analysis:

| ppm | Interpretation | |
|---|---|---|
| 1.12 (d) | | |
| 1.21 (t) | C(CH₃)—C ; CH₃—C—O | 6H |
| 2.60–2.06 (m) | methine and methylene protons | 3H |
| 4.10 (q) | CH₃—CH₂—O—C(=O)— | 2H |
| 5.10–4.94 | HC=CH₂ | 2H |
| 5.94–5.03 | HC=CH₂ | 1H |

Infrared Analysis:
910, 990, 1025, 1050, 1090, 1140, 1180, 1250, 1275, 1345, 1370, 1430, 1640, 1730, 2880, 2900, 2940, 2980.

Note 1: Primol is a registered trademark identifying a hydrocarbon mineral oil produced by Exxon Incorporation of Linden, N.J.
Note 2: Ionol is a registered trademark identifying the compound 2,6,-di-tert-butyl-4-methyl-phenol.

EXAMPLE IV

Hydrogenation of Ethyl-2-Methyl-3,4-Pentadienoate Using a Raney Nickel Catalyst Thereby Preparing Mixtures of Ethyl-2-Methyl-Cis-3-Pentenoate and Ethyl-2-Methyl Pentanoate Reaction:

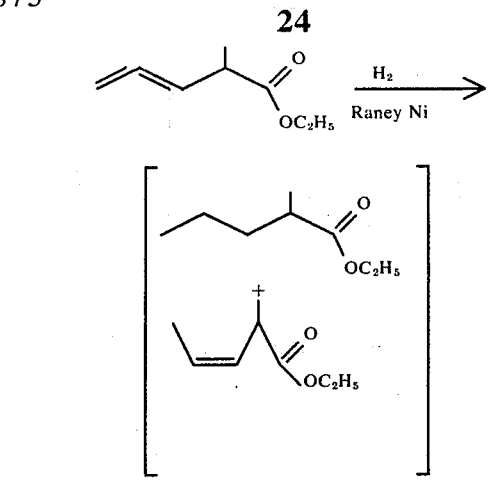

Into a 2-liter autoclave fitted by means of pressure tubing to a hydrogen-containing cylinder is added the following materials:

| Ingredient | Quantity |
|---|---|
| Ethyl-2-methyl-3,4-pentadienoate prepared according to the process of Example I | 283.3 g |
| Raney nickel | 14 g |

Figure 5:
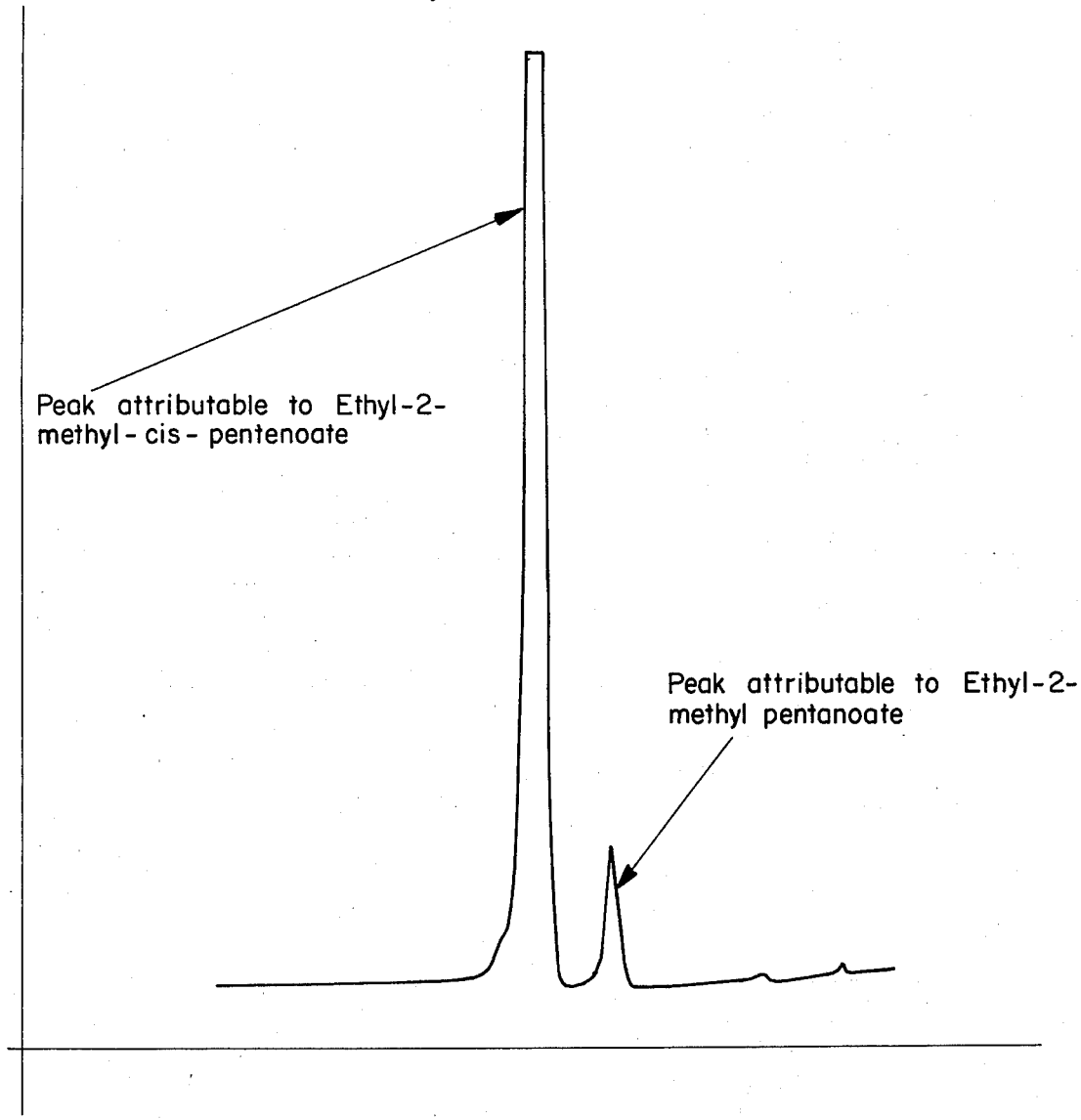

The autoclave is closed and, while stirring and maintaining the temperature at 20° C (using external cooling), the reaction mass is pressurized to 20 pounds per square inch gauge (psig) using hydrogen. The pressure is maintained using the hydrogen feed at 20 pounds per square inch and the temperature is maintained at 20° C over a period of 3 hours. At the end of the 3-hour period, the autoclave is opened and the reaction mass is filtered. GLC analysis indicates that the reaction is complete. According to GLC, NMR, IR and mass spectral analyses, the reaction mass contains 65% ethyl-2-methyl-cis-3-pentenoate and 35% ethyl-2-methyl-pentanoate. The GLC curve is set forth in FIG. 5.

After adding 5.0 grams of Primol and 0.1 grams of Ionol the filtered reaction mass is distilled on a 36 inch × 1.5 inch Goodloe distillation column. The following fractions are collected:

| Fraction No. | Vapor Temp. | Liquid Temp. | Vacuum (mm Hg Pressure) | Weight of Fraction | Reflux Ratio |
|---|---|---|---|---|---|
| 1 | 50° C | 55° C | 20.0 | 7.4 g | 19:1 |
| 2 | 50 | 55 | 20.0 | 8.5 | 19:1 |
| 3 | 50 | 55 | 20.0 | 8.8 | 19:1 |
| 4 | 50 | 55 | 20.0 | 14.5 | 19:1 |
| 5 | 50 | 55 | 20.0 | 15.9 | 19:1 |
| 6 | 50 | 55 | 20.0 | 11.4 | 19:1 |
| 7 | 50 | 55 | 20.0 | 12.5 | 19:1 |
| 8 | 50 | 55 | 20.0 | 11.5 | 19:1 |
| 9 | 50 | 55 | 20.0 | 11.7 | 19:1 |
| 10 | 50 | 55 | 20.0 | 11.2 | 19:1 |
| 11 | 50 | 55 | 20.0 | 22.2 | 19:1 |
| 12 | 50 | 55 | 20.0 | 11.0 | 19:1 |
| 13 | 50 | 55 | 20.0 | 11.8 | 19:1 |
| 14 | 50 | 55 | 20.0 | 12.7 | 19:1 |
| 15 | 52 | 56–57 | 20.0 | 10.0 | 19:1 |
| 16 | 52 | 57 | 20.0 | 10.9 | 19:1 |
| 17 | 52 | 57 | 20.0 | 9.5 | 19:1 |
| 18 | 52 | 57 | 20.0 | 7.0 | 19:1 |
| 19 | 52 | 57 | 20.0 | 3.7 | 19:1 |
| 20 | 53 | 58 | 20.0 | 2.6 | 19:1 |
| 21 | 53 | 58 | 20.0 | 5.8 | 19:1 |
| 22 | 53 | 59 | 20.0 | 5.5 | 19:1 |
| 23 | 53 | 63 | 20.0 | 6.0 | 19:1 |
| 24 | 53 | 95 | 20.0 | 7.5 | 19:1 |

-continued

| Fraction No. | Vapor Temp. | Liquid Temp. | Vacuum (mm Hg Pressure) | Weight of Fraction | Reflux Ratio |
|---|---|---|---|---|---|
| 25 | 53 | 140 | 20.0 | 3.8 | 19:1 |

Fractions 16–25 are bulked and GLC, NMR and IR analyses indicate that this bulked fraction contains 5.7% ethyl-2-methyl-pentanoate and 93.8% ethyl-2-methyl-cis-3-pentenoate. This material has a fresh strawberry taste with light, rubbery off-notes. When this fraction is re-distilled in order to eliminate the saturated ester which counteracts the delicate strawberry taste of the unsaturated cis ester, the material is an excellent, fresh strawberry flavor additive. The 100% cis material has a fruity, strawberry, pineapple aroma with rum, and honey undertones suitable as a food flavor, perfumery, and tobacco flavor additive.

IR, NMR and mass spectral analyses for the saturated ester, the ethyl-2-methyl pentanoate is as follows:

Mass Spectral Analysis: Parent peak, then in order of decreasing intensity:

m/e = 144/43, 102, 29, 27, 71, 74.

NMR Analysis:

| ppm | Interpretation | |
|---|---|---|
| 0.88 (t) | $CH_3-(CH_2)_n-$ | 3H |
| 1.08 (d) | $CH_3-\overset{H}{\underset{|}{C}}-$ | 6H |
| 1.21 (t) | $CH_3-C-O-\overset{O}{\underset{\|}{C}}-$ | |
| 1.70–1.34 (m) | $-CH_2-$ | 4H |
| 2.40 (m) | $Me-\overset{H}{\underset{|}{C}}-$ | 1H |
| 4.08 (q) | $Me-CH_2-O-\overset{O}{\underset{\|}{C}}-$ | 2H |

Infrared Analysis:
    740 cm⁻¹, 850, 1035, 1050, 1080, 1145, 1180, 1245, 1350, 1375, 1460, 1730, 2880, 2940, 2960.

The IR, NMR and mass spectral data for the unsaturated cis ester, ethyl-2-methyl-cis-3-pentenoate, is identical to that set forth in Example III.

EXAMPLE V

Preparation of Ethyl-2-Methyl-Cis-3-Pentenoate: Ethyl-2-Methyl-4-Pentenoate and Ethyl-2-Methyl Pentanoate by Hydrogenation of 2-Methyl-3,4-Pentadienoate using a Raney Nickel Catalyst Reaction:

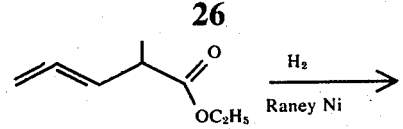

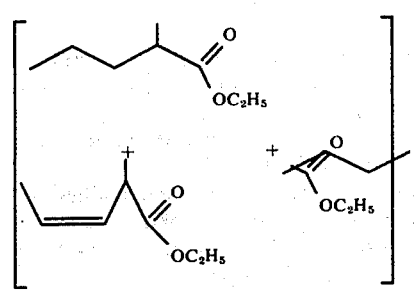

Into a 500 cc autoclave fitted by means of pressure tubing to a hydrogen-containing cylinder is added the following materials:

| Ingredient | Quantity |
|---|---|
| ethyl-2-methyl-3,4-pentadienoate prepared according to the process of Example | 187 grams |
| Raney nickel | 7 grams |

The autoclave is closed, and, while stirring and maintaining the temperature at 20°–30° C (using external cooling) the reaction mass is pressurized to 50 pounds per square inch gauge (psig) using hydrogen. The pressure is maintained using the hydrogen feed at 50 pounds per square inch, and the temperature is maintained at 20°–30° C over a period of 5½ hours. After 2½ hours, 1 gm mole of hydrogen was absorbed in the reaction mass; and GLC analysis shows the presence of the following materials:

| | |
|---|---|
| ethyl-2-methyl pentanoate | 2% |
| ethyl-2-methyl-4-pentenoate | 25.7% |
| ethyl-2-methyl-cis-3-pentenoate | 62.5% |
| ethyl-2-methyl-3,4-pentadienoate | 8.9% (starting material) |

The reaction is continued for another hour by repressurization using the hydrogen feed up to 50 psig. At the end of the 3½ hours, 1–19 gm moles of hydrogen is absorbed by the reaction mass, and the autoclave is opened and again GLC analysis is carried out. GLC analysis indicates the following composition in the reaction mass after 3½ hours:

| | |
|---|---|
| ethyl-2-methyl-pentanoate | 11% |
| ethyl-2-methyl-4-pentenoate | 19.7% |
| ethyl-2-methyl-cis-3-pentenoate | 68% |

The autoclave is then closed and repressurized with hydrogen to 50 psig and the reaction is continued for another 2 hours, at which time 1.5 gm moles of hydrogen (total) is absorbed by the reaction mass. At the end of the 2 hour period, the autoclave is again opened and GLC analysis indicates the following:

| | |
|---|---|
| ethyl-2-methyl pentanoate | 35% |

| | |
|---|---|
| ethyl-2-methyl-cis-3-pentenoate | 65% |

At the 5½ hour reaction time, it is significant to note that no ethyl-2-methyl-4-pentenoate is present in the reaction mass.

Figure 6:
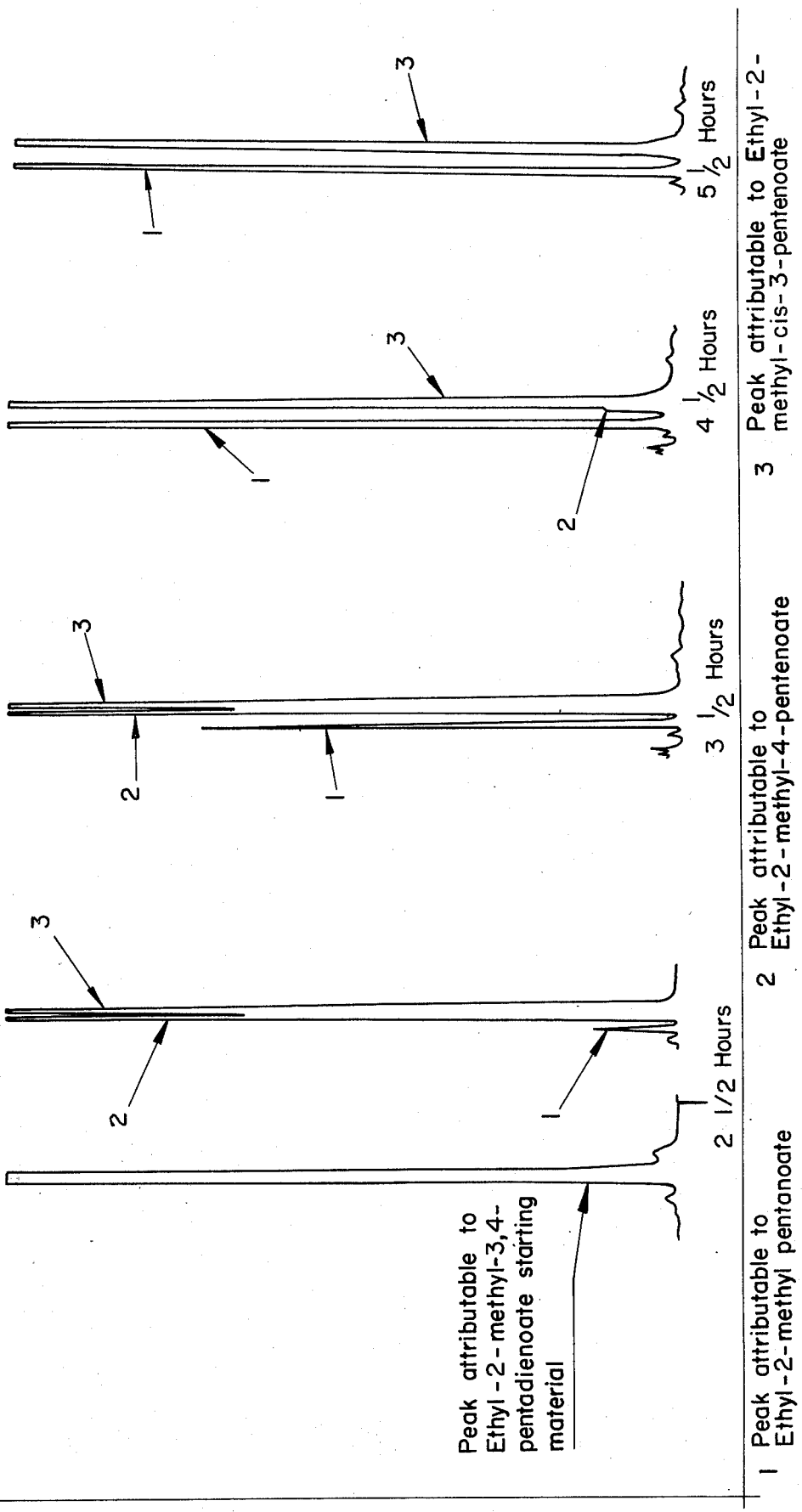

GLC analysis at 2½ hours, 3½ hours and 5½ hours are set forth in FIG. 6.

The final mixture is filtered and distilled in a 36 inch × 1½ inch Goodloe column after adding thereto 5.0 grams of Primol and 0.1 grams of Ionol yielding the following fractions:

| Fraction No. | Vapor Temp. | Liquid Temp. | Pressure (mm Hg) | Weight | Reflux Ratio |
|---|---|---|---|---|---|
| 1 | 50° C | 55° C | 20.0 | 7.4 | 19:1 |
| 2 | 50 | 55 | 20.0 | 8.5 | 19:1 |
| 3 | 50 | 55 | 20.0 | 8.8 | 19:1 |
| 4 | 50 | 55 | 20.0 | 14.5 | 19:1 |
| 5 | 50 | 55 | 20.0 | 15.9 | 19:1 |
| 6 | 50 | 55 | 20.0 | 11.4 | 19:1 |
| 7 | 50 | 55 | 20.0 | 12.5 | 19:1 |
| 8 | 50 | 55 | 20.0 | 11.5 | 19:1 |
| 9 | 50 | 55 | 20.0 | 11.7 | 19:1 |
| 10 | 50 | 55 | 20.0 | 11.2 | 19:1 |
| 11 | 50 | 55 | 20.0 | 22.2 | 19:1 |
| 12 | 50 | 55 | 20.0 | 11.0 | 19:1 |
| 13 | 50 | 55 | 20.0 | 11.8 | 19:1 |
| 14 | 50 | 55 | 20.0 | 12.7 | 19:1 |
| 15 | 52 | 56–57 | 20.0 | 10.0 | 19:1 |
| 16 | 52 | 57 | 20.0 | 10.9 | 19:1 |
| 17 | 52 | 57 | 20.0 | 9.5 | 19:1 |
| 18 | 52 | 57 | 20.0 | 7.0 | 19:1 |
| 19 | 52 | 57 | 20.0 | 3.7 | 19:1 |
| 20 | 53 | 58 | 20.0 | 2.6 | 19:1 |
| 21 | 53 | 58 | 20.0 | 5.8 | 19:1 |
| 22 | 53 | 59 | 20.0 | 5.5 | 19:1 |
| 23 | 53 | 63 | 20.0 | 6.0 | 19:1 |
| 24 | 53 | 95 | 20.0 | 7.5 | 19:1 |
| 25 | 53 | 140 | 20.0 | 3.8 | 19:1 |

Fraction No. 22 is analyzed using NMR, GLC and mass spectral analysis as being 95% ethyl-2-methyl-cis-3-pentenoate and 5% ethyl-2-methyl pentanoate. This fraction is then redistilled in order to substantially eliminate the saturated ester which counteracts the delicate strawberry taste of the unsaturated cis ester. The resulting cis ester is an excellent, fresh strawberry additive having a fruity, strawberry, pineapple aroma with rum and honey undertones suitable as a food flavor, medicinal product flavor, chewing gum flavor, perfumery adjuvant and tobacco additive. The IR, NMR and mass spectral data for the saturated and for the unsaturated esters are identical to those set forth in Examples II and III supra.

When the above process is repeated without sampling for GLC analysis at the 2½ hour and 3½ hour intervals, after 5½ hours, 1.48 gm moles of hydrogen is absorbed in the reaction mass and GLC analysis shows the following:

| | |
|---|---|
| ethyl-2-methyl pentanoate | 38% |
| ethyl-2-methyl-cis-3-pentenoate | 61.4% |

When the above procedure is repeated with sampling at 3½ hours and 4 hours, the following results are obtained:

i. 3½ hours:

hydrogen uptake 1.4 gm moles percentage of ethyl-2-methyl pentanoate is 27% percentage of ethyl-2-methyl-4-pentenoate is 4% ethyl-2-methyl-cis-3-pentenoate 68% ii. 4 hours:

hydrogen uptake 1.5 gm moles percentage ethyl-2-methyl pentanoate is 36% percentage ethyl-2-methyl-cis-3-pentenoate is 63.6%.

EXAMPLE VI

A. Preparation of Trihexyl-Orthopropionate

Reaction:

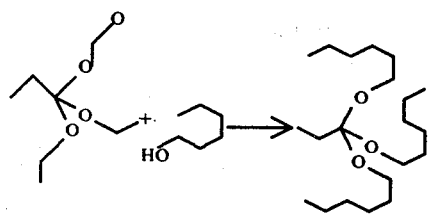

Into a 3-liter distillation flask, equipped with a 2 inch splash column, reflux condenser and fraction cutter, the following materials are placed:

| Ingredients | Amount |
|---|---|
| Triethyl ortho propionate | 528 g (3 moles) |
| n-Hexyl alcohol | 1530 g (15 moles) |
| p-Toluene sulfonic acid | 3.4 g (0.02 moles) |
| Primol | 20 g |

The reaction mass is heated to a pot temperature of 150° C at atmospheric pressure and 398.9 g of "light'-'(ethanol) fractions distills off. The reaction mass is then placed under vacuum and the reaction product is distilled over as a colorless liquid at 1.3 mm Hg pressure and a temperature of 140°–171° C. The yield is 930.7 g (87.6%) and the product is a compound having the structure:

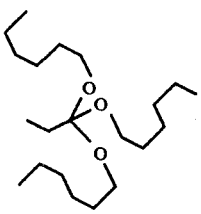

B. Preparation of n-Hexyl-2-Methyl-3,4-Pentadienoate

Reaction:

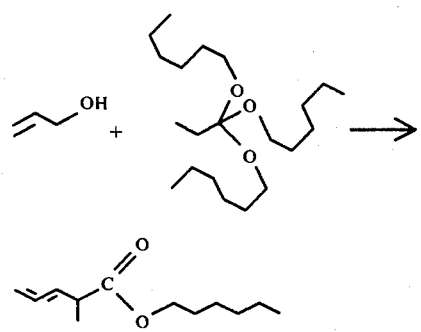

Into a 2-liter autoclave, the following materials are placed:

| Ingredient | Amount |
|---|---|
| n-Hexyl orthopropionate (produced according to the process of Part A) | 1240 grams (3.5 moles) |
| 2-Propyn-1-ol | 196 grams (3.5 moles) |
| Propionic acid | 30 grams |

The autoclave is closed and the reaction mass is heated to 120°–130° C (a heatup time of 50 minutes). The reaction mass is maintained at a temperature of between 120°–130° C for a period of 5 hours. At the end of this 5-hour period, the autoclave is cooled to room temperature. The reaction mixture is decanted and 35 g of sodium bicarbonate is then added to the reaction mass in order to neutralize the propionic acid. 40 g of Primol is added and the resulting reaction product is distilled to yield ten fractions. Fractions 6, 7 and 8 distilling 95°–101° C and 2.2–2.5 mm Hg (to yield 481.3 g of a crude product) are combined and fractionally distilled on a 12 inch × 1 inch Goodloe column after adding thereto 10.0 g Primol and 0.1 g Ionol, as follows:

| Fraction No. | Vapor Temperature | Liquid Temperature | Pressure (mm Hg) | Weight of Fraction | Reflux Ratio |
|---|---|---|---|---|---|
| 1 | 44 | 72–87 | 3.5–3.4 | 40.0 g | 9:1 |
| 2 | 47 | 97 | 3.4 | 33.9 | 9:1 |
| 3 | 77 | 101 | 3.4 | 36.5 | 9:1 |
| 4 | 88 | 104 | 3.4 | 20.3 | 9:1 |
| 5 | 89 | 104 | 3.4 | 33.9 | 9:1 |
| 6 | 89 | 104 | 3.4 | 29.1 | 9:1 |
| 7 | 80–89 | 105–115 | 3.5–3.4 | 33.5 | 9:1 |
| 8 | 89 | 115 | 3.2 | 33.4 | 9:1 |
| 9 | 89 | 117 | 3.1 | 84.1 | 3:1 |
| 10 | 90 | 119 | 3.2 | 83.6 | 3:1 |
| 11 | 86–89 | 110–112 | 3.2 | 32.5 | 9:1 |
| 12 | 89 | 125 | 3.2 | 74.4 | 3:1 |
| 13 | 88 | 155 | 3.3 | 32.4 | 3:1 |
| 14 | 110 | 195 | 3.3 | 44.5 | 3:1 |

Fractions 9 and 10 are bulked and the resulting material is confirmed by IR, NMR and mass spectral analyses to have a purity greater than 99% and to have the structure:

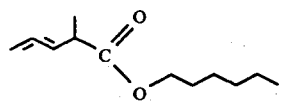

It has a tagette-oil-like, apple taste and aroma with pear and fatty nuances.

Figure 7:
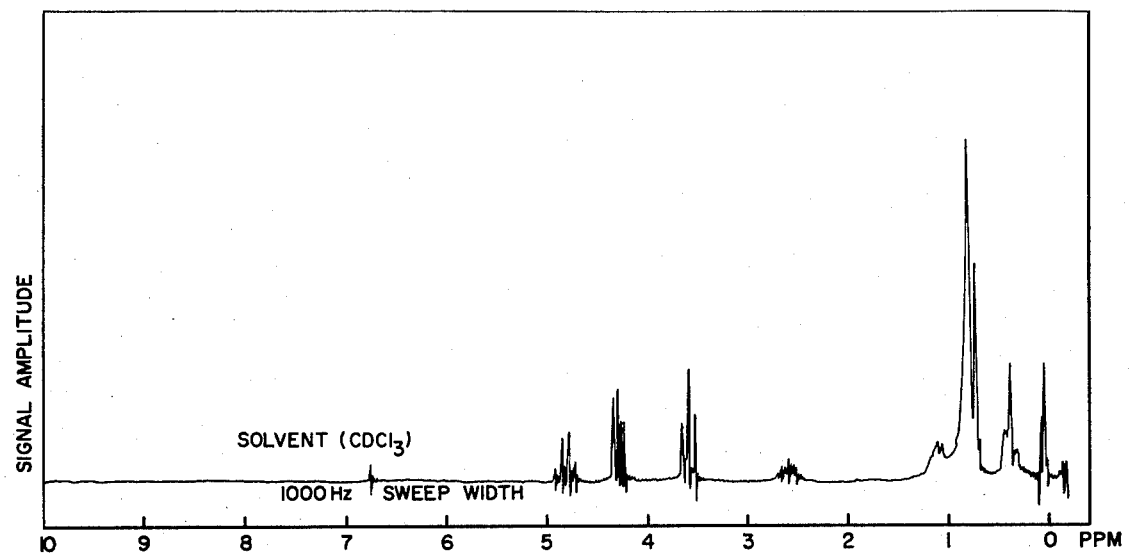
Figure 8:
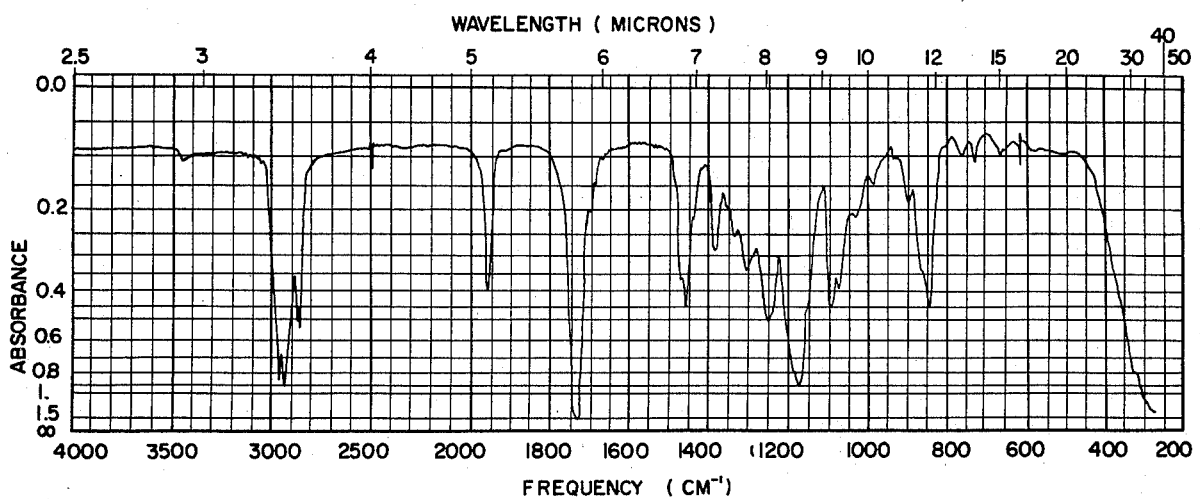

Analyses:
1. The nuclear magnetic resonance spectrum is illustrated in FIG. 7.
2. The infrared spectrum is illustrated in FIG. 8.
3. Mass spectral analysis: Molecular ion; then in order of decreasing intensity: 196/43, 41, 112, 97, 67, 85.
4. NMR analysis:

| ppm | Interpretation | |
|---|---|---|
| 0.88 ppm (t) | $CH_3-CH_2-$ | 3H |
| 1.24 ppm (d) | $CH_3-\underset{C=O}{\underset{|}{\overset{C=}{\underset{|}{C}}}}-$ | 11H |
| 1.28 (broad s) | $-CH_2-$ | |
| 1.62 (m) | $-CH_2-C-O-$ | |
| 3.10 (m) | $=C-\underset{H}{\overset{|}{C}}-C=O$ | 1H |
| 4.08 (t) | $-CH_2-O-\overset{O}{\underset{||}{C}}$ | 2H |
| 4.76 (7 doublets) | $H_2C=C=C-\left(\begin{array}{c}J=3Hz\\6Hz\end{array}\right)$ | 2H |
| 5.32 (q) | $-C=C=CH$ | 1H |

5. Infrared analysis:
845 cm⁻¹
1065
1085
1175
1250
1455
1730
1960
2860
2880
2940
2960

EXAMPLE VII

Hydrogenation of n-Hexyl-2-Methyl-3,4-Pentadienoate Using a Lindlar Catalyst Thereby Preparing Mixtures of n-Hexyl-2-Methyl-Cis-3-Pentenoate and n-Hexyl-2-methyl-4-Pentenoate Reaction:

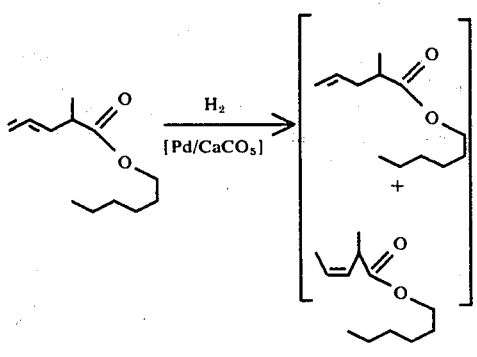

Into a 2-liter autoclave, the following ingredients are placed:

| Ingredient | Quantity |
|---|---|
| n-hexyl-2-methyl-3,4-pentadienoate produced according to the process of Example | .98 grams (0.5 moles) |
| palladium-on-calcium catalyst (Lindlar catalyst) | 1.0 grams |

The autoclave is connected by means of pressure tubing to a hydrogen-containing cylinder. The autoclave is then sealed, and while adding hydrogen into the autoclave from the hydrogen-containing cylinder and maintaining the pressure within the autoclave at 50 psig, the reaction mass is stirred during the hydrogenation and over a period of 40 minutes. At the end of the 40-minute period, the autoclave is opened, and the reaction mass is filtered. GLC analysis shows total conversion to n-hexyl-2-methyl-cis-3-pentenoate and n-hexyl-2-methyl-4-pentenoate. The GLC curve is set forth in FIG. 9.

EXAMPLE VIII

Preparation of Isobutyl-2-Methyl-3,4-Pentadienoate

Reaction:

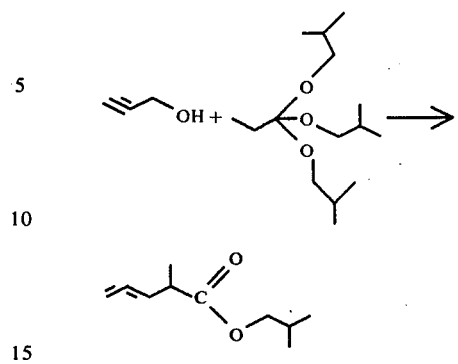

Into a 2-liter autoclave, the following materials are placed:

| Ingredient | Amount |
|---|---|
| Triisobutyl orthopropionate | 696.9 grams |
| 2-Propyn-1-ol | 151 grams |
| Propionic acid | 17 grams |

The autoclave is closed and the reaction mass is heated to 140° C over a period of 50 minutes. The reaction mass is then maintained at a temperature of 140° C for a period of 4 hours. At the end of this 4-hour period, the autoclave is cooled to room temperature. 20 g of sodium bicarbonate is then added to the reaction mass in order to neutralize the propionic acid. 30 g of Primol is added and the reaction mass is fractionally distilled on a 2 inch splash column yielding the following fractions:

| Fraction No. | Vapor Temperature | Liquid Temperature | Pressure (mm Hg) | Weight of Fraction | %Product |
|---|---|---|---|---|---|
| 1 | 38–25° C | 45–27° C | 30–8.7 | 182.1 | 2 |
| 2 | 30 | 44 | 6.0 | 192.5 | 4.1 |
| 3 | 70 | 77 | 6.0 | 55.4 | 14.6 |
| 4 | 72 | 80 | 6.8 | 213.9 | 93.3 |
| 5 | 72 | 200 | 7.9 | 131.6 | 97 |

10 g Primol and 0.1 g Ionol are then added to the resulting distillate which is vacuum distilled yielding isobutyl-2-methyl-3,4-pentadienoate as follows:

| Fraction No. | Vapor Temperature | Liquid Temperature | Pressure (mm Hg) | Weight of Fraction | Reflux Ratio |
|---|---|---|---|---|---|
| 1 | 41–70° C | 77–83° C | 7.3–7.7 | 15.4 | 19:1–19:1 |
| 2 | 72 | 78 | 7.9 | 12.9 | 19:1 |
| 3 | 72 | 78 | 7.8 | 15.1 | 19:1 |
| 4 | 72 | 78 | 7.8 | 22.8 | 9:1 |
| 5 | 72 | 78 | 7.8 | 30.3 | 4:1 |
| 6 | 72 | 78 | 7.8 | 39.6 | 4:1 |
| 7 | 72 | 78 | 7.8 | 48.3 | 4:1 |
| 8 | 72 | 78 | 7.8 | 47.3 | 4:1 |
| 9 | 72 | 78 | 7.8 | 46.0 | 4:1 |
| 10 | 72 | 81 | 7.8 | 43.6 | 4:1 |
| 11 | 72 | 204 | 7.8 | 7.7 | 4:1 |

Fractions 4–10 are bulked and the resulting material (greater than 99% purity via GLC) is confirmed by NMR and IR analyses to have the structure:

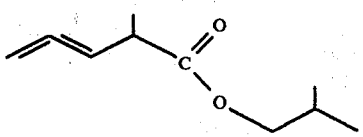

Nuclear Magnetic Resonance Analysis:

| ppm | Interpretation | |
|---|---|---|
| 0.92 ppm (d) | CH₃\C(H)/CH₃ — | 6H |
| 1.26 ppm (d) | C=C / CH₃—CH / C=O | 3H |
| 1.92 ppm (m) | H₃C\C(H)/ H₃C | 1H |
| 3.12 ppm (m) | O=C—C(H)—C=C | 1H |
| 3.87 ppm (d) | —CH₂—O—C(=O)— | 2H |
| 4.79 ppm (d of d)* | H₂C=C=C—C | 2H |
| *doublet of doublets | | |
| 5.33 ppm (q) | H₂C=C=C(H)—C | 1H |

Figure 10:
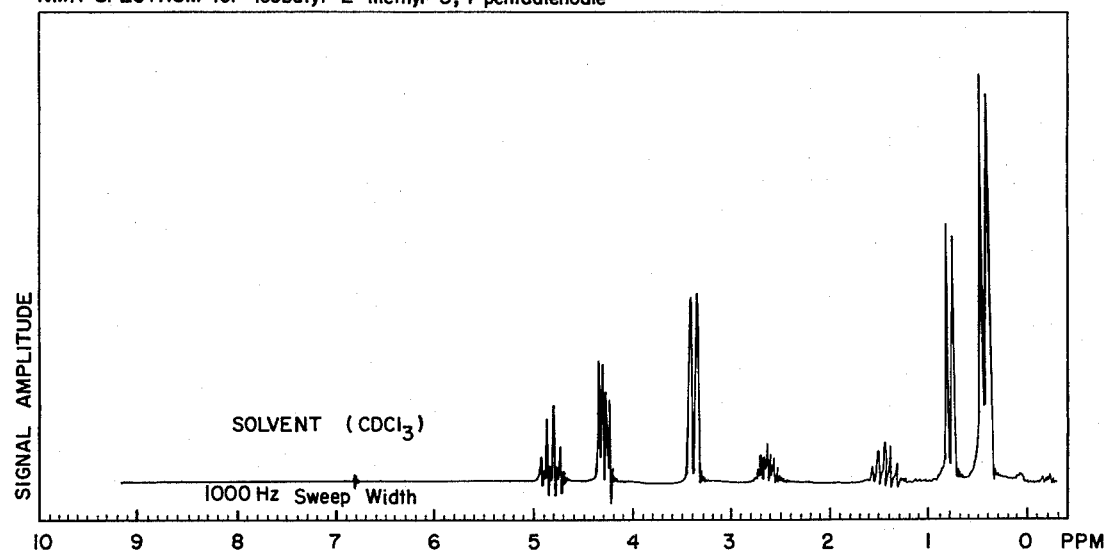

The nuclear magnetic resonance spectrum is set forth in FIG. 10.

Mass Spectral Data
168/41, 67, 57, 39, 29, 112, 97.

Infra Red Analysis:
Peaks
840 cm⁻¹
985
1030
1065
1085
1170
1240
1300
1365
1375
1455
1470
1730
1955
2870
2940
2960

Figure 11:
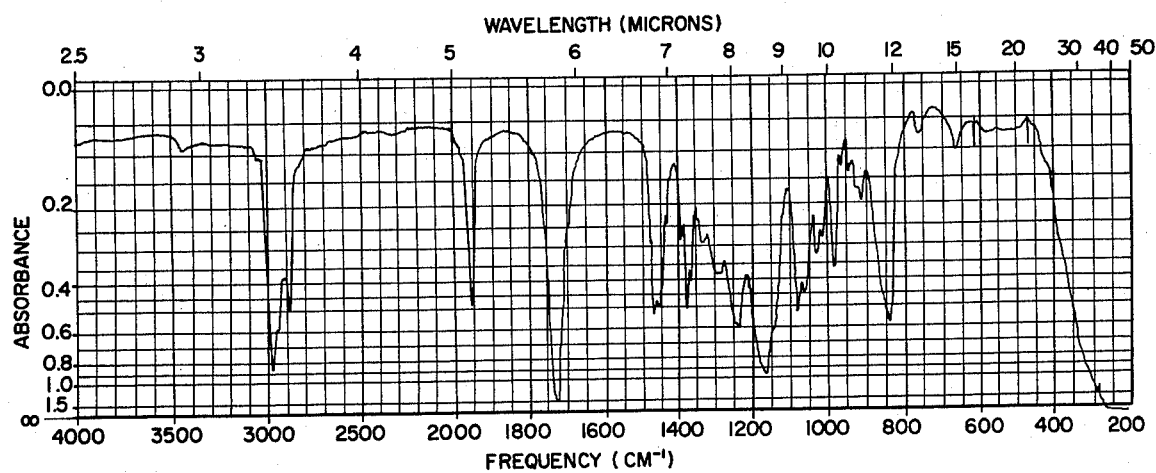

The infra-red spectrum is set forth in FIG. 11.

EXAMPLE IX

Hydrogenation of Isobutyl-2-Methyl-3,4-Pentadienoate Using a Lindlar Catalyst Thereby Preparing Mixtures of Isobutyl-2-Methyl-Cis-3-Pentenoate and Isobutyl-2-Methyl-4-Pentenoate Reaction:

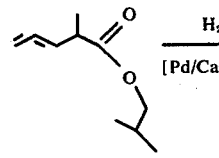

Into a 2-liter autoclave, the following ingredients are placed:

| Ingredient | Quantity |
|---|---|
| isobutyl-2-methyl-3,4-pentadienoate produced according to the process of Example VIII | 168 grams |
| palladium-on-calcium carbonate catalyst (Lindlar catalyst) | 2.0 grams |

The autoclave is connected by means of pressure tubing to a hydrogen-containing cylinder. The autoclave is then sealed and while adding hydrogen into the autoclave from the hydrogen-containing cylinder and maintaining the pressure within the autoclave at 45–50 psig, the reaction mass is stirred. During the hydrogenation and over a one-hour period, the reaction mass is maintained at temperatures of from 50°–82° C by means of the application of cooling. At the end of the one-hour period, the autoclave is opened and the reaction mass is filtered. GLC analysis indicates that all of the material is converted to a mixture of isobutyl-2-methyl-4-pentenoate and isobutyl-2-methyl-cis-3-pentenoate. The GLC analysis is illustrated in FIG. 12.

The resulting material is confirmed by NMR, IR and mass spectral analyses to have the following structures:

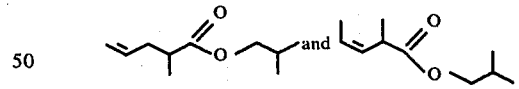

Nuclear Magnetic Resonance Analysis:

| ppm | Interpretation |
|---|---|
| 0.88 | H₃C\C(H)/H₃C— |
| 1.20 | CH₃—C(H)—C=O / C=C |
| 1.64 | CH₃—C(H)=C— |
| 1.91 | HC—C(=O)— |
| 3.44 | =C—C(H)—C(=O)— |

-continued

| ppm | Interpretation |
|---|---|
| 3.84 | $-CH_2-O-\overset{O}{\underset{\|}{C}}-$ |
| 5.07 | $-\underset{\|}{C}=CH_2$ |
| 5.48 | $HC=CH$ and $HC=CH_2$ |

Infra-red analysis (cm$^{-1}$):
990, 1015, 1020, 1040, 1170, 1240, 1325, 1375, 1465, 1725, 2280, 2960.
Mass spectral analysis:
170/41, 69, 57, 29, 27, 39.

EXAMPLE X

Preparation of 2-Methyl-Cis-3-Pentenoic Acid

Into a 250 ml flask equipped with stirrer, thermometer, reflux condenser and heating mantle the following materials are added:

| | |
|---|---|
| 50% aqueous NaOH | 60 grams |
| methanol | 50 grams |

The reaction mass heats up to 55° C and is cooled using external cooling to 20° C. Ethyl-2-cis-3-pentenoate (prepared according to Example V; bulked fractions 20–22) is then added dropwise with stirring to the reaction mass while maintaining same at a temperature of 20° C. The addition takes place over a period of 30 minutes. After addition is completed, the reaction mass is stirred for another 30 minutes. 22 grams of concentrated sulfuric acid is then added dropwise to the reaction mass with stirring. 150 ml of 5% hydrochloric acid is added bringing the reaction mixture to a pH of 4.

The reaction mass is then stirred for a period of 15 minutes and is extracted with three 150 ml portions of diethyl ether. The extracts are combined and evapoated and the concentrated material is rushed over to yield the following fractions:

| Fraction No. | Vapor Temperature | Pot Temperature | Vacuum | Weight of Fraction | % Product |
|---|---|---|---|---|---|
| 1 | 80 | 94 | 7.5 | 0.7 | >90% |
| 2 | 89 | 99 | 7.8 | 3.0 | >90% |
| 3 | 90 | 140 | 8.2 | 23.6 | >99% |
| 4 | 90 | 200 | 8. | 1.1 | >99% |

NMR, IR and Mass spectral analyses confirm the resultant material to be 2-methyl-cis-3-pentenoic acid having a purity greater than 99%.

EXAMPLE XI

Strawberry Flavor

The following basic strawberry flavor is prepared:

| Ingredients | Parts by Weight |
|---|---|
| p-Hydroxybenzylacetone | 2 |
| Vanillin | 15 |
| Maltol | 20 |
| Ethyl methylphenyl glycidate | 15 |
| Benzyl acetate | 20 |

-continued

| Ingredients | Parts by Weight |
|---|---|
| Ethyl butyrate | 10 |
| Methyl cinnamate | 5 |
| Methyl anthranilate | 5 |
| Alpha-ionone | 1 |
| Gamma-undecalactone | 2 |
| Diacetyl | 2 |
| Anethole | 1 |
| Cis-3-hexenol | 17 |
| Ethanol (95% aqueous) | 385 |
| Propylene glycol | 500 |

To one-third of this flavor, ethyl-2-methyl pentenoate mixture (prepared according to Example III; bulked fractions 12–31) is added at the rate of 1%. To another third of this flavor the 2-methyl pentenoic acid mixture (prepared according to Example X) is added at the rate of 8%. The third portion of this flavor is kept "as is." The three flavors thus produced are compared at the rate of 0.005% (50 ppm) in water by a bench panel.

The flavor containing the ethyl-2-methyl pentenoate mixture is found to have a more fresh natural strawberry-like aroma and taste than the basic flavor formulation. The flavor containing the 2-methyl pentenoic acid mixture was found also to have a more natural strawberry-like aroms and taste; especially a preferred, sweet, fresh, strawberry-like aroma, and is preferred over the basic flovor formulation.

EXAMPLE XII

The following concentrate is prepared:

| Ingredient | Percent |
|---|---|
| Geraniol | 1.00 |
| Ethyl methyl phenyl glycidate | 3.50 |
| Isobutyl-2-methyl pentenoate mixture (prepared according to the process of Example IX) | 5.00 |
| Vanillin | 5.50 |
| Ethyl pelargonate | 13.00 |
| Isoamyl acetate | 14.00 |
| Ethyl butyrate | 58.00 |
| | 100.0 |

EXAMPLE XIII

Another concentrate is prepared as follows:

| Ingredient | Percent |
|---|---|
| Naphthyl ethyl ether | 1.0 |
| Vanillin | 2.5 |
| Ethyl methyl phenyl glycidate | 3.0 |
| Isobutyl-2-methyl pentenoate mixture (prepared according to the process of Example IX) | 5.0 |
| Ethyl acetate | 9.5 |
| Isoamyl acetate | 12.0 |
| Ethyl butyrate | 26.0 |
| Isoamyl butyrate | 41.0 |

-continued

| Ingredient | Percent |
|---|---|
| | 100.0 |

EXAMPLE XIV

The concentrate prepared in Example XII is dissolved in 4 volumes of propylene glycol and the mixture is added to a hard candy melt at the rate of 1.5 oz. of the concentrate solution per 100 lbs. of melt. After the finished candy has been produced, it is found to have an excellent strawberry flavor. When the candy is compared with candy made under the same conditions, but without the isobutyl-2-methyl pentenoate mixture prepared according to the process of Example IX in the concentrate, it is found to have an inferior strawberry flavor.

EXAMPLE XV

The propylene glycol solution of the concentrate as prepared in Example XIV is added to a simple syrup at the rate of one-eighth oz. per gallon of syrup. The syrup is acidified by the addition of 1.5 oz. of 50% aqueous citric acid solution to each gallon of syrup. A carbonated beverage is prepared by admixing 1 oz. of the flavored, acidified syrup with 5 oz. of carbonated water. The beverage so prepared has an excellent fresh strawberry flavor and is found to be markedly superior to a beverage prepared in the same manner but without the isobutyl-2-methyl-pentenoate mixture prepared according to the process of Example IX/

EXAMPLE XVI

The flavor concentrate prepared in Example XII is admixed with gum arabic and in the proportion of 7 lbs. of concentrate to 28 lbs. of gum arabic in 65 lbs. of water, and the aqueous mixture is spray-dried. The flavor concentrate-carrier combination so obtained is then added to a gelatin dessert mix in the ratio of 1 oz. of spray-dried material to 100 lbs. of dessert mix powder. The gelatin dessert produced from the mix has an excellent strawberry flavor is markedly superior to a gelatin dessert prepared in the same manner without the isobutyl-2-methyl pentenoate mixture prepared according to the process of Example IX in the concentrate.

EXAMPLE XVII

Strawberry Fragrance

The following mixture is prepared:

| Ingredient | Parts by Weight |
|---|---|
| Ethyl pelargonate | 5 |
| Ethyl laurate | 20 |
| Cinnamyl isobutyrate | 10 |
| Diacetyl 10% | 5 |
| Cuminic acetate | 10 |
| Peach aldehyde coeur | 50 |
| Ethyl isobutyrate | 100 |
| Ethyl isovalerate | 50 |
| Ethyl heptoate | 10 |
| para hydroxy phenyl butanone | 3 |
| Ethyl acetate | 2 |
| Beta ionone | 10 |
| Palatone | 2 |
| Vanillin | 5 |
| Ethyl vanillin | .2 |
| Ethyl methyl phenyl glycidate | 75 |
| Isobutyl-2-methyl pentenoate | 10 |

| Ingredient | Parts by Weight |
|---|---|
| mixture (prepared according to the process of Example IX) | |
| Ethyl-2-methyl pentenoate mixture (prepared according to the process of Example III; bulked fractions 12–31) | 3 |

The ethyl-2-methyl pentenoate mixture prepared according to the process of Example III (bulked fractions 12–31) imparts the extreme green, sweet topnote to this strawberry fragrance. The isobutyl-2-methyl pentenoate mixture prepared according to the process of Example IX imparts a green, tart, seed note to the strawberry aroma.

EXAMPLE XVIII

Tobacco Formulation

A tobacco mixture is produced by admixing the following materials:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 100 and 200 ppm of 2-methyl-cis-3-pentenoic acid produced according to the process of Example X. The control cigarettes not containing the 2-methyl pentenoic acid mixture produced according to the process of Example X and the experimental cigarettes which contain the 2-methyl-cis-3-pentenoic acid produced according to the process of Example X are evaluated by paired comparison and the results are as follows:

The experimental cigarettes are found to be, on smoking, more aromatic in aroma.

In the smoke, the experimental cigarettes are found to be more aromatic, sweeter, more bitter, less harsh in the mouth and throat and leave a slight sweet chemical mouth coating effect similar to Turkish tobacco. All cigarettes are evaluated for smoke flavor with a 20 mm cellulose acetate filter.

The 2-methyl-cis-3-pentenoic acid produced according to the process of Example X enhances the tobacco-like taste and aroma of the blended cigarette and gives the cigarette a Turkish-like character.

EXAMPLE XIX

Preparation of Soap Composition

One hundred grams of soap chips are mixed with one gram of the perfume composition of Example XVII until a substantially homogeneous composition is obtained. The perfumed soap composition manifests an excellent strawberry character with a green, sweet, tart and seed nuances.

EXAMPLE XX

Preparation of a Detergent Composition

A total of 100 g of a detergent powder is mixed with 0.15 g of the perfume composition of Example XVII until a substantially homogeneous composition is obtained. This composition has an excellent strawberry fragrance.

EXAMPLE XXI

Preparation of a Cosmetic Powder Composition

A cosmetic powder is prepared by mixing in a ball mill, 100 g of talcum powder with 0.25 g of ethyl-2-methyl pentenoate mixture prepared according to Example III (bulked fractions 12–31). It has an excellent sweet, green, strawberry aroma.

EXAMPLE XXII

Perfumed Liquid Detergent

Concentrated 0.10%, detergents with a fruity, chamomile odor are prepared containing 0.10%, 0.15% and 0.20% of isobutyl-2-methyl pentenoate mixture prepared according to Example IX. They are prepared by adding and homogeneously mixing the appropriate quantity of isobutyl-2-methyl pentenoate mixture in the liquid detergent. The detergents all possess a green, tart, strawberry fragrances, the intensity increasing with greater concentrations of isobutyl-2-methyl pentenoate mixture.

EXAMPLE XXIII

Preparation of a Cologne and Handkerchief perfume

The ethyl-2-methyl pentenoate mixture prepared according to the process of Example III (bulked fractions 12–31) is incorporated in a cologne at a concentration of 2.5% in 85% aqueous ethanol; and into a handkerchief perfume at a concentration of 20% (in 95% aqueous ethanol). A distinct and definite sweet, green, strawberry fragrance is imparted to the cologne and to the handkerchief perfume.

EXAMPLE XXIV

The following mixture is prepared:

| Ingredient | Parts by Weight |
| --- | --- |
| Ethyl acetoacetate | 3 |
| Ethyl laurate | 10 |
| Cinnamyl isobutyrate | 3 |
| Cinnamyl isovalerate | 5 |
| Diacetyl | 2 |
| Heliotropyl acetate | 20 |
| Peach aldehyde coeur | 100 |
| Ethyl butyrate | 200 |
| Ethyl isovalerate | 20 |
| Ethyl heptanoate | 1 |
| Dulcinyl | 5 |
| 2(para-hydroxyphenyl)-3- | 2 |

-continued

| Ingredient | Parts by Weight |
| --- | --- |
| butanone | |
| Ethyl acetate | 1 |
| Beta-ionone | 10 |
| Palatone | 2 |
| Ethyl vanillin | 1 |
| Ethyl-3-methyl-3-phenyl glycidate | 150 |
| n-hexyl-2-methyl pentenoate mixture prepared according to the process of Example VII | 5 |

The n-hexyl-2-methyl pentenoate mixture prepared according to the process of Example VII imparts a fruity, chamomile, peppery, floral note to this strawberry fragrance.

EXAMPLE XXV

Preparation of a Cosmetic Powder Composition

A cosmetic powder is prepared by mixing in a ball mill, 100 g of talcum powder with 0.25 g of n-hexyl-2-methyl pentenoate mixture prepared according to Example VII. It has an excellent fruity, chamomile aroma.

EXAMPLE XXVI

Perfumed Liquid Detergents

Concentrated liquid detergents with a fruity, chamomile odor are prepared containing 0.10%, 0.15% and 0.20% of the n-hexyl-2-methyl pentenoate of Example VII. They are prepared by adding and homogeneously mixing the appropriate quantity of n-hexyl-2-methyl pentenoate mixture in the liquid detergent. The detergents all possess a fruity, chamomile fragrance, the intensity increasing with greater concentrations of n-hexyl-2-methyl pentenoate mixture of Example VII.

EXAMPLE XXVII

Preparation of a Cologne and Handkerchief Perfume

The composition of Example XXIV is incorporated in a cologne at a concentration of 2.5% in 85% aqueous ethanol; and into a handkerchief perfume at a concentration of 20% (in 95% aqueous ethanol). The use of the n-hexyl-2-methyl pentenoate mixture in the composition of Example XXIV affords a distinct and definite strong strawberry aroma with a chamomile note to the handkerchief perfume and cologne.

EXAMPLE XXVIII

Preparation of Soap Composition

One hundred grams of soap chips are mixed with one gram of n-hexyl-2-methyl pentenoate mixture of Example VII until a substantially homogeneous composition is obtained. The perfumed soap composition manifests an excellent strawberry aroma with fruity and green notes and a chamomile nuance.

What is claimed is:

1. A composition of matter consisting essentially of at least two 6-carbon-atom-containing carboxylic acids or lower alkyl esters thereof and containing:
   a. More than 60% by weight of 2-methyl-cis-3-pentenoic acid or a lower alkyl ester thereof; and
   b. Less than 40% by weight of at least one compound selected from the group consisting of:
      i. 2-methyl-4-pentenoic acid or a lower alkyl ester thereof; and ii. 2-methyl pentanoic acid or a lower alkyl ester thereof produced by the process comprising the steps of:

i. Intimately contacting with hydrogen gas, an alkyl-2-methyl-3,4-pentadienoate having the structure:

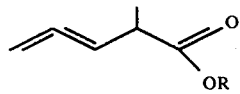

in the presence of a hydrogenation catalyst selected from the group consisting of:
a. Raney nickel;
b. Palladium-on-carbon; and
c. Palladium-on-calcium carbonate at a temperature in the range of from about 10° C up to about 100° C; a hydrogen pressure in the range from about 5 psig up to about 80 psig, the concentration of said catalyst, based on the weight of alkyl-2-methyl-3,4-pentadienoate, being from about 0.1% up to about 10%;

ii. Physically recovering a chemical composition from the reaction mass which contains at least 60% by weight of an alkyl-2-methyl-cis-3-pentenoate having the structure:

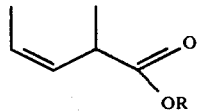

wherein R is alkyl having from 1 up to 6 carbon atoms.

2. A composition of matter consisting essentially of at least two 6-carbon-atom-containing carboxylic acids and containing:
a. More than 60% by weight of 2-methyl-cis-3-pentenoic acid; and
b. Less than 40% by weight of at least one compound selected from the group consisting of:
i. 2-methyl-4-pentenoic acid; and
ii. 2-methyl pentanoic acid produced by the process comprising the steps of:

i. Intimately contacting with hydrogen gas an alkyl-2-methyl-3,4-pentadienoate having the structure:

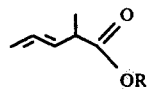

in the presence of a hydrogenation catalyst selected from the group consisting of:
a. Raney nickel;
b. Palladium-on-carbon; and
c. Palladium-on-calcium carbonate at a temperature in the range of from about 10° C up to about 100° C; a hydrogen pressure in the range of from about 5 psig up to about 80 psig, the concentration of said catalyst, based on the weight of said alkyl-2-methyl-3,4-pentadienoate being from about 0.1% up to about 10%;

ii. Physically recovering a chemical composition from the reaction mass which contains at least 60% by weight of an alkyl-2-methyl-cis-3-pentenoate having the structure:

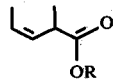

wherein R is an alkyl group containing from 1 up to 6 carbon atoms; and iii. Intimately admixing the resulting chemical composition with a hydrolysis agent selected from the group consisting of:
a. An aqueous solution of an alkali metal hydroxide; and
b. An alcoholic solution of an alkali metal hydroxide and (iv) Physically recovering a chemical composition from the reaction mass which comprises at least 60% by weight of 2-methyl-cis-3-pentenoic acid having the structure:

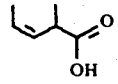

* * * * *